(12) United States Patent
Lambros et al.

(10) Patent No.: US 9,808,425 B2
(45) Date of Patent: Nov. 7, 2017

(54) TARGETED LIPOSOMES IN CANCER THERAPY

(75) Inventors: Maria Polikandritou Lambros, Pomona, CA (US); Ying Huang, Pomona, CA (US); Hari Chandana Mulamalla, Monroe Township, NJ (US)

(73) Assignee: WESTERN UNIVERSITY OF HEALTH SCIENCES, Pomona, CA (US)

( * ) Notice: Subject to any disclaimer, the term of this patent is extended or adjusted under 35 U.S.C. 154(b) by 902 days.

(21) Appl. No.: 14/240,753

(22) PCT Filed: Sep. 10, 2012

(86) PCT No.: PCT/US2012/054463
§ 371 (c)(1),
(2), (4) Date: Jun. 9, 2014

(87) PCT Pub. No.: WO2013/036931
PCT Pub. Date: Mar. 14, 2013

(65) Prior Publication Data
US 2015/0157571 A1    Jun. 11, 2015

Related U.S. Application Data

(60) Provisional application No. 61/532,430, filed on Sep. 8, 2011.

(51) Int. Cl.
*A61K 9/127* (2006.01)
*A61K 47/48* (2006.01)
*A61K 31/704* (2006.01)

(52) U.S. Cl.
CPC .......... *A61K 9/1271* (2013.01); *A61K 31/704* (2013.01); *A61K 47/48815* (2013.01)

(58) Field of Classification Search
CPC ...................................................... A61K 9/127
See application file for complete search history.

(56) References Cited

U.S. PATENT DOCUMENTS

| | | | |
|---|---|---|---|
| 2003/0119735 A1* | 6/2003 | Fischer | A61K 47/48238 514/1.2 |
| 2008/0058265 A1* | 3/2008 | Rezaie | C12N 9/6464 514/1.4 |
| 2008/0226917 A1 | 9/2008 | Zhong et al. | |

FOREIGN PATENT DOCUMENTS

| | | |
|---|---|---|
| JP | S63 2921 A | 1/1988 |
| WO | 87/04622 A1 | 8/1987 |

(Continued)

OTHER PUBLICATIONS

Trosko, J.E., in Mutation Research, 480-481, pp. 219-229, 2001.*

(Continued)

*Primary Examiner* — Gollamudi Kishore
(74) *Attorney, Agent, or Firm* — J.A. Lindeman & Co., PLLC

(57) ABSTRACT

The invention provides pharmaceutical compositions containing a vehicle for the targeted delivery of therapeutic and diagnostic agents for the treatment of hyperproliferative diseases. The targeting component of the vehicle is a cystine molecule that is coupled to the cargo component, which can be either a therapeutic or diagnostic agent or to a nanoparticle composition that contains the therapeutic agent or diagnostic. The invention also provides methods of treating hyperproliferative disorders by targeting hyperproliferative disease cells for the targeted delivery of a therapeutic or diagnostic agent.

8 Claims, 36 Drawing Sheets

(56) References Cited

FOREIGN PATENT DOCUMENTS

| WO | 2003/101425 | A2 |   | 12/2003 |
|----|-------------|----|---|---------|
| WO | 2005/065724 | A1 |   | 7/2005  |
| WO | 2009/017624 |    | * | 2/2009  |
| WO | 2010/095940 | A2 |   | 8/2010  |
| WO | 2010/125068 | A2 |   | 11/2010 |

OTHER PUBLICATIONS

Filpula et al., "Releasable PEGylation of proteins with customized linkers", Advanced Drug Delivery Review, 2008, vol. 60, pp. 29-49.
International Search Report and Written Opinion for PCT International Application No. PCT/US2012/054463, dated Nov. 23, 2012.
International Preliminary Report on Patentability of PCT International Application No. PCT/US2012/054463, dated Mar. 12, 2014.
Daniels et al., "The transferrin receptor and the targeted delivery of therapeutic agents against cancer," Biochimica et Biophysica Acta, 2012, vol. 1820, pp. 291-317.
Kamagami et al., "Penetration Enhancement Across a Model Membrane by Liposomally Entrapped Drugs Using N,N-Diacylcystine as a Bilayer Lipid," FEBS Letters, vol. 281, No. 1-2, Apr. 1, 1991, pp. 133-136.
Schott et al., "Palmitoyl Derivatives of I-cysteine, cysteamine, 1-cystine, cystamine and Their Incorporation into the Bilayers of Unilamellar Liposomes," Biochemica et Biophysica Acta, vol. 940., No. 1, May 9, 1988, pp. 127-135.
Supplemental European Search Report in Application No. EP 12 83 510, dated Jul. 9, 2015.
English Abstract of JPS632921 A.

* cited by examiner

A

B

TARGETED LIPOSOMES IN CANCER THERAPY

CROSS-REFERENCE TO RELATED APPLICATIONS

Priority is claimed to U.S. Application Ser. No. 61/532,430 filed 8 Sep. 2011, the entire disclosure of which is incorporated herein by reference.

FIELD OF THE INVENTION

The invention relates to compositions and methods for the targeted delivery of therapeutic and diagnostic agents, including targeted intracellular delivery therapeutic and diagnostic agents, and to the treatment of hyperproliferative diseases.

BACKGROUND

The effectiveness of treatment for hyperproliferative disorders, (e.g., malignant and benign tumors), with chemotherapeutic drugs is limited by several significant barriers, including: i) nonspecific toxicity of the drugs for normal as well as tumor tissues; ii) inefficiency of drug delivery to target cells; and iii) inappropriate release of the drug. Consequently, many chemotherapeutic drugs are characterized as having low therapeutic indexes, and thus, relatively high doses of the drugs are required, which, in turn, results in serious side effects. As such, the development of additional targeted delivery systems for the delivery of chemotherapeutic drugs to target cells would resolve many of the undesirable aspects of chemotherapy. This invention addresses that need by targeting drugs to cells that express abnormally high levels of the plasma cell membrane components of the system $x_c^-$ heterodimeric amino acid transporter specific for cystine/glutamate exchange.

System $x_c^-$ imports L-cystine into the intracellular compartment of a cell, which requires L-cystine for the synthesis of glutathione (L-γ-glutamyl-L-cysteinylglycine, referred to herein as "GSH"), an antioxidant that is important for cell survival under hypoxic conditions, such as those that exist in a tumor environment. The structure of System $x_c^-$ imports is composed of SLC7A11, a catalytic subunit that gives the transporter its specificity for cystine, and SLC3A2, a regulatory subunit. SLC7A11 and SLC3A2 are also known in the field as xCT and 4F2hc/CD98, respectively.

Because tumor cells, and other abnormally rapidly dividing or differentiating cells require greater amounts of GSH to handle higher levels of oxidative stress, such cells more highly express system $x_c^-$ components for the importation of cystine than do normal cells under normal conditions. As such, the invention takes advantage of the increased expression of system $x_c^-$ components by hyperproliferative cells by providing drug and diagnostic delivery vehicles that incorporate cystine to mediate the delivery vehicles to the system $x_c^-$ components of target cells.

SUMMARY OF THE INVENTION

The invention provides pharmaceutical compositions for the targeted delivery of therapeutic and diagnostic agents for the treatment of hyperproliferative diseases. In various embodiments, the invention provides a vehicle for the targeted delivery of a therapeutic agent or a diagnostic agent, or both that contains a targeting component and a cargo component. The targeting component is a cystine molecule that is coupled to the cargo component, which can be a therapeutic agent or diagnostic agent or both, or to a nanoparticle composition that contains a therapeutic agent and or a diagnostic agent or both. In various embodiments, the nanoparticle composition is a liposome-encapsulated therapeutic or diagnostic agent.

The invention also provides methods of treating hyperproliferative disorders by targeting hyperproliferative disease cells for the intracellular delivery of therapeutic or diagnostic agents, or both. In various embodiments, the method of the invention administers an effective amount of a vehicle of the invention to accomplish intracellular delivery of a therapeutic or a diagnostic agent, the vehicle comprising a cystine molecule coupled to a cargo for intracellular delivery, wherein the cargo is a therapeutic agent ingredient or a composition comprising a therapeutic or diagnostic agent, or both.

BRIEF DESCRIPTION OF THE TABLES

Figure 1:
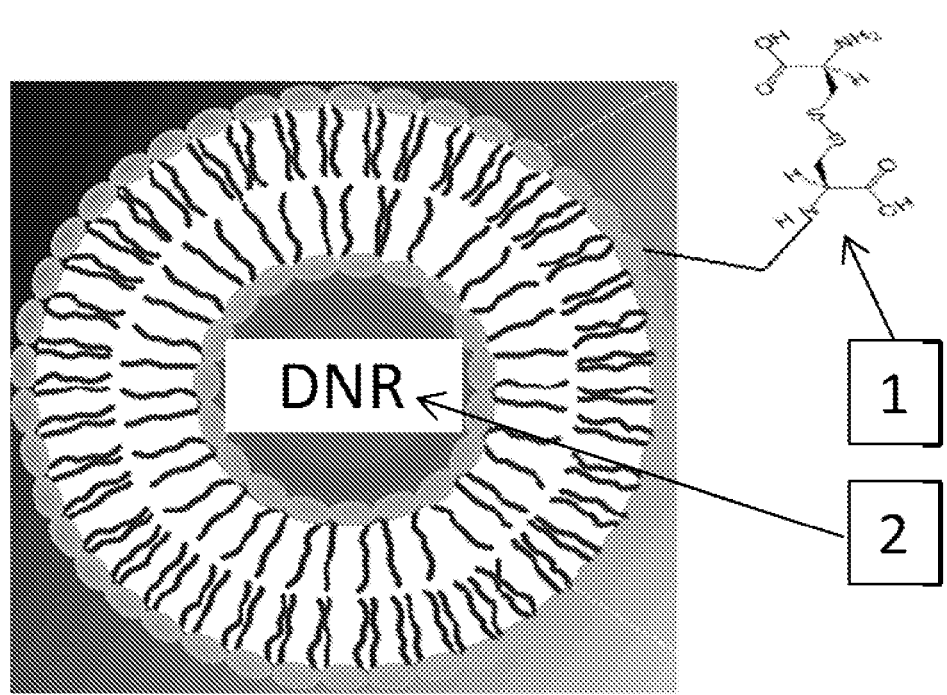
FIG. 1 depicts the structure of daunorubicin (DNR) encapsulated by a cystine-conjugated liposome. The figure depicts a Natta projection of the cystine molecule.
Figure 2:
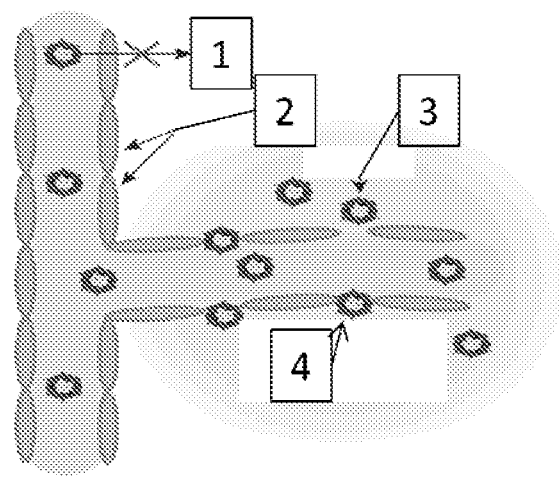
FIG. 2 depicts the enhanced permeability and retention of nanoparticles, e.g., Liposomes in cancerous tissue. (1) depicts nanoparticles that are unable to penetrate the endothelium of vessels in healthy tissue. (2) depicts a normal endothelium. (3) and (4) depict the extravasation of nanoparticles from vessels in tumor tissue.
Figure 3:
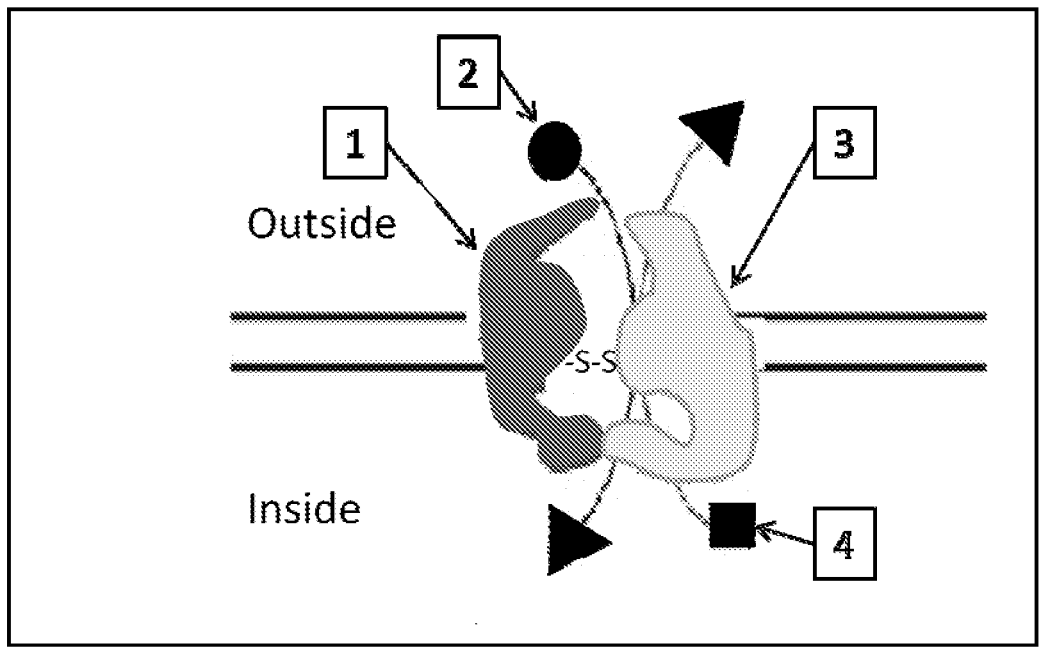
FIG. 3 depicts a functional representation of the $x_c^-$ cystine/glutamate transporter system. (1) represents the SLC3A2 subunit of the transporter, (2) represents the cellular importation of cystine by the transporter, (3) represents the SLC7A11 subunit of the transporter, and (4) represents the exportation of glutamate by the transporter.

Table 1 shows the $IC_{50}$ (μM DNR) concentrations for free DNR, liposoml DNR, cystine liposomal DNR, and cystine liposomal DNR in the presence of glutamate. The concentration values were derived from the cell viability curves of FIGS. 12A and 13A.

DETAILED DESCRIPTION

The invention provides vehicles and methods for the targeted delivery of therapeutic and diagnostic agents. More particularly, a vehicle of the invention comprises one or more cystine molecules that are coupled to a cargo, which comprises a therapeutic agent or diagnostic agent, or both, to form a "vehicle of the invention." A vehicle of the invention can be delivered to a target cell that expresses components of the cystine-specific system $x_c^-$ heterodimeric amino acid transporter, which is formed by a heterodimer of the subunits, SLC7A11 and SLC3A2, and is referred to, hereafter, as a "transporter". Generally, transporters are more highly expressed by cells under conditions of abnormal oxidative stress, such as those that frequently exist for hyperproliferative cells, and thus, is are effective disease cell targets for vehicles the invention based on the specific interaction between cystine and the transporter. A cargo can be a therapeutic or diagnostic agent or a composition comprising a therapeutic agent, diagnostic agent, or combinations thereof.

In various embodiments, a vehicle of the invention delivers a therapeutic or diagnostic agent to the intracellular compartment of a cell. While not wishing to be bound by any particular theory, cellular uptake of a therapeutic agent or diagnostic agent from a vehicle of the invention can be accomplished by the interaction of the one or more cystines of the vehicle of the invention with the transporter. In various embodiments, the interaction between a cystine of a vehicle of the invention and the transporter initiates a series of cellular events that cause the target cell to endocytose a vehicle of the invention or various components of the vehicle, e.g., a therapeutic or diagnostic agent. In certain embodiments of the invention the endocytosis event that is initiated by the interaction between the cystine of a vehicle of the invention and transporter is an energy-dependent pinocytotic event.

The Cystine Component

As used herein, cystine is understood to be a dimeric amino acid formed by the oxidation of two cysteine residues that covalently link to make a disulfide bond. In various embodiments of the invention, cystine is L-cystine. Cystines may be attached to the cargo by using methods known in the art, including making modifications to the cargo to include a functional group that is reactive with a cystine, (e.g., a liposome cargo molecule may be oxidized, and the cystine attached to the surface of the liposome by performing a reductive amination reaction). Methods to directly attach cystines to the cargo component of the vehicle of the invention by a chemical bond can be found in Hermanson, G, "Bioconjugate Techniques," $1^{st}$ ed. Academic Press (1996), and Hermanson, G, "Bioconjugate Techniques," $2^{nd}$ ed. Elsevier Inc. (2008) which is incorporated in its entirety herein.

In various other embodiments of the invention, cystine may also be indirectly attached to the cargo thorough a linking group, such as, but not limited to a polyethylene glycol (PEG), diacid linkers such as succinic acid, malic acid, etc; di-aldehydes such as gludaraldehide, hydroxy acids where the hydroxy group of the hydroxy acid forms an ester with the cystine carboxylate, and the carboxylic acid of the linker forms an ester with the PEG hydroxy group, and amino acid linkers such as e-amino-caproic acid where the amino group of the linker forms an amide with the cystine carboxylate and the carboxylic acid of the linker forms an ester with the PEG hydroxy group. Furthermore, the amino group of cystine can be used to form a covalent bond with the linkers, e.g., a PEG or any other linker molecule. In addition to linking cystines to the cargo component of a vehicle of the invention, PEG molecules also allow the conjugate to evade clearance of the vehicle of the invention by the immune system of a recipient of a treatment. More specifically, the mononuclear phagocytic system can be overcome by incorporation of PEG into a vehicle. The invention does not particularly limit PEG for its molecular weight, but PEG molecules that are attached to a vehicle of the invention typically have molecular weights of from about 400 to about 10,000 Daltons. However, the invention accommodates PEG molecules that are up to 100,000 Daltons or more.

The Cargo Component

As stated above, the cargo of a vehicle of the convention can also be a composition comprising a therapeutic agent. For example, a composition that is a cargo according to the invention, can be a nanoparticle that comprises a therapeutic agent that is in a composition with a material, such as, but not limited to: a lipid, (e.g., liposomes); a cyclodextrin; a biocompatabile polymer, (e.g., polylactic acid (PLA), polyglycolic acid (PGA, and polymers specified on the FDA GRAS list, which is incorporated by reference), lactic acid/glycolic acid copolymer (PLGA)); or a biological material (e.g., albumin).

With respect to lipid compositions, the invention does not particularly limit the selection of lipid components that are provided. However, examples of lipids are selected from, but not limited to, cholesterol, phosphatidylcholines, phosphatidylglycerols, phosphatidylethanolamines, phosphatidylserines, phosphatidic acid, sterylamines, cationic lipids, tissue derived phosphatidylcholine, phosphatidylinositol, lactosylceramide, galactose cerebroside, gangliosides, lipids having periodate-oxidazable components containing vicinal hydroxyls, and glycolipids. Liposomes of the invention may also contain a pharmaceutically acceptable stabilizer and/or antioxidant depending on the administration route. Non-limiting examples of the stabilizer include sugars such as glycerol, mannitol, sorbitol, lactose, and sucrose. When a sterol such as cholesterol is used for the additional lipid constituent of the membrane, such sterol also acts as a stabilizer.

In addition to a stabilizer, a liposome cargo composition of the invention may also comprise a pharmaceutically acceptable additive depending on the administration route. Examples of such additive include water, physiological saline, pharmaceutically acceptable organic solvent, collagen, polyvinyl alcohol, polyvinylpyrrolidone, carboxyvinyl polymer, sodium carboxymethyl cellulose, poly(sodium acrylate), sodium alginate, water soluble dextran, sodium carboxymethyl starch, pectin, methylcellulose, ethylcellulose, xanthan gum, gum arabic, casein, gelatin, agar, diglycerin, propylene glycol, polyethylene glycol, vaseline, paraffin, stearyl alcohol, stearic acid, human serum albumin (HSA), mannitol, sorbitol, lactose, PBS, in vivo degradable polymer, serum-free medium, pharmaceutically acceptable surfactant, and any combination thereof.

The term "loading," as it is to be understood herein, is basically used to designate the state in which the therapeutic agent is encapsulated in the closed space of the liposome. However, it may also include the state in which a part of the therapeutic agent is confined in the membrane or the state in which the therapeutic agent is attached to the exterior surface of the membrane. The desired amount of the therapeutic agent that is loaded, i.e., encapsulated, in the liposome varies depending on the type of the drug.

In various embodiments, the cargo of a vehicle of the invention is a liposome-encapsulated therapeutic agent, wherein the surface of the liposome can be modified by the attachment of a hydrophilic macromolecule. Such a modification may be accomplished by a reaction to attach a derivative, such as a phospholipid derivative or a cholesterol derivative of a PEG. For example, a PEGI derivative or an aqueous solution of the PEG derivative may be added to the liposome dispersion to produce a liposome having the PEG chain only on the exterior surface of the liposome. Alternatively, a modified liposome may be produced by producing a liposome containing a membrane-constituting lipid such as a phospholipid having a reactive functional group by the method commonly used in the art, and thereafter adding a PEG having one activated end to the exterior solution of the liposome for binding of such PEG to the membrane-constituting lipid such as the phospholipid having the functional group. In the procedures as described above, various techniques are available for use in producing a liposome having the desired size ("Liposome Technology Liposome Preparation and Related Techniques" 2nd edition, edited by G. Gregoriadis, Vol. I-III, CRC Press) which is herein incorporated by reference.

With respect to a vehicle of the invention that comprises cargo that comprises a polymer encapsulated therapeutic agent, such nanoparticles are based on the ability of a molecule of a therapeutic agent to combine itself with one or more cyclodextrin molecules through the creation of low-energy chemical bonds, that are, hence, non-covalent such as to form an inclusion complex. The existence of this complex results from the formation of an equilibrium between a) the free forms of the therapeutic agent and cyclodextrin and b) the inclusion complex. It is quantitatively characterized by its stability constants.

The invention does not particularly limit the selection of polymer components that can be included in the cargo component of the vehicle of the invention. However, the invention provides for at least one or more polymers that are selected from, but not limited to, a polycation polymer, a polyanion polymer, or non-ionic polymer. A polycationic or polyanionic polymer has at least one site that bears a positive or negative charge, respectively. A non-limiting set of polymers that are suitable for the cargo component of the vehicle of the invention include, but are not limited to the cyclical oligosaccharides, in particular, from among the cyclodextrins which may be neutral or charged, native (cyclodextrins α, β, γ, δ, and ε), branched or polymerized, or even chemically modified, for example, by substitution of one or more hydroxypropyls by groups such as alkyls, aryls, arylalkyls, glycosidics, or by etherification, esterification with alcohols or aliphatic acids.

The cyclodextrin-containing polymers of the invention may be linear, branched or grafted. As used herein, the term "linear cyclodextrin-containing polymer" refers to a polymer comprising (α, β, γ, δ, and ε) cyclodextrin molecules, or derivatives thereof which are inserted within a polymer chain.

With respect to a vehicle of the invention that comprises a cargo component that comprises albumin, the invention typically provides human serum albumin (HSA). HSA is a highly soluble globular protein of $M_r$ 65 K and consists of 585 amino acids. HSA is the most abundant protein in the plasma and accounts for 70-80% of the colloid osmotic pressure of human plasma. The amino acid sequence of HSA contains a total of 17 disulphide bridges, one free thiol (Cys 34), and a single tryptophan (Trp 214). Human serum albumin (HSA) has multiple hydrophobic binding sites (a total of eight for fatty acids, an endogenous ligand of HSA) and binds a diverse set of drugs, especially neutral and negatively charged hydrophobic compounds (Goodman et al., The Pharmacological Basis of Therapeutics, Twelfth ed, McGraw-Hill New York (2011)). Two high affinity binding sites have been proposed in subdomains IIA and IIIA of HSA, which are highly elongated hydrophobic pockets with charged lysine and arginine residues near the surface which function as attachment points for polar ligand features (see, e.g., Fehske et al., Biochem. Pharmcol., 30, 687-92 (1981), Vorum, Dan. Med. Bull., 46, 379-99 (1999), Kragh-Hansen, Dan. Med Bull., 1441, 131-40 (1990), Curry et al., Nat. Struct. Biol., 5, 827-35 (1998), Sugio et al., Protein. Eng., 12, 439-46 (1999), He et al., Nature, 358, 209-15 (1992), and Carter et al., Adv. Protein. Chem., 45, 153-203 (1994)). Paclitaxel (Abraxane™) and propofol have been shown to bind HSA (see, e.g., Paal et al., Eur. J. Biochem., 268(7), 2187-91 (2001), Purcell et al., Biochim. Biophys. Acta, 1478(1), 61-8 (2000), Altmayer et al., Arzneimittelforschung, 45, 1053-6 (1995), and Garrido et al., Rev. Esp. Anestestiol. Reanim., 41, 308-12 (1994)). In addition, docetaxel has been shown to bind to human plasma proteins (see, e.g., Urien et al., Invest. New Drugs, 14(2), 147-51 (1996)). While not wishing to be bound to any particular theory, it is believed that the inclusion of proteins such as albumin in compositions that form the cargo component of the vehicle of the invention can result in a reduction in side effects associated with administration of the therapeutic agent that is due, at least in part, to the binding of human serum albumin to any free drug that is present in the composition.

Therapeutic Agents

As stated above, a cargo, according to the invention, can be a therapeutic agent itself or a composition comprising a therapeutic agent wherein the therapeutic agent can be introduced into cells by attaching it to at least one cystine. The therapeutic agent may be a single therapeutic agent or may be a combination of different therapeutic agents. As understood in one embodiment, a therapeutic agent, i.e., a drug, includes, but is not limited to, small organic molecules, inorganic molecules, therapeutic peptides and proteins, antibodies, radioisotopes, siRNA and nucleic acids for gene therapy, and toxins that are functional in intracellular compartments, and that can be used to treat, diagnose, inhibit, or prevent the progression of a disease, i.e., an abnormal condition affecting the body, including hyperproliferative diseases such as cancer and nonmalignant tumors. Thus, in various embodiments, the vehicle of the invention comprises a chemotherapeutic agent.

Examples of classes of therapeutic agents that are provided by the invention include, but are not limited to (i) kinase inhibitors such as e.g. Imatinib (Glivec™), ZD-1839/Gefitinib Wessel, Bay43-9006 (Sorafenib, Nexavar™), SU11248/Sunitinib (Sutent™) or OSI-774/Erlotinib (Tarceva™), Dasatinib (SprycellM), Lapatinib (Tykerb™), or, see also below, Vatalanib, Vandetanib (Zactima™) or Pazopanib; (ii) proteasome inhibitors such as PS-341/Bortezumib (Velcade™); (iii) heat shock protein 90 inhibitors like 17-allylaminogeldanamycin (17-AAG); (iv) vascular targeting agents (VTAs) like combretastin A4 phosphate or AVE8062/AC7700 and anti-angiogenic drugs like the VEGF antibodies, such as Bevacizumab (Avastin™), or KDR tyrosine kinase inhibitors such as PTK787/ZK222584 (Vatalanib) or Vandetanib (Zactima™) or Pazopanib; (v) monoclonal antibodies such as Trastuzumab (Herceptin™) or Rituximab (MabThera/Rituxan™) or Alemtuzumab (Campath™) or Tositumomab (Bexxar™) or C225/Cetuximab (Erbitux™) or Avastin (see above) or Panitumumab as well as mutants and conjugates of monoclonal antibodies, e.g. Gemtuzumab ozogamicin (Mylotarg™) or Ibritumomab tiuxetan (Zevalin™), and antibody fragments; (vi) oligonucleotide based therapeutics like G-3139/Oblimersen (Genasense™); (vii) Toll-like receptor/TLR 9 agonists like Promune™, TLR 7 agonists like Imiquimod (Aldara™) or Isatoribine and analogues thereof, or TLR 7/8 agonists like Resiquimod as well as immunostimulatory RNA as TLR 7/8 agonists; (viii) protease inhibitors (ix) hormonal therapeutics such as anti-estrogens (e.g. Tamoxifen or Raloxifen), anti-androgens (e.g. Flutamide or Casodex), LHRH analogs (e.g. Leuprolide, Goserelin or Triptorelin) and aromatase inhibitors.

Examples of particular therapeutic agents that are provided by the invention include, but are not limited to 5 FU, actinomycin D, Abarelix, Abciximab, Aclarubicin, Adapalene, Alemtuzumab, Altretamine, Aminoglutethimide, Amiprilose, Amrubicin, Anastrozole, Ancitabine, Artemisinin, Azathioprine, Basiliximab, Bendamustine, Bevacizumab, Bexxar, Bicalutamide, Bleomycin, Bortezomib, Broxuridine, Busulfan, Campath, Capecitabine, Carboplatin, Carboquone, Carmustine, Cetrorelix, Chlorambucil, Chlormethine, Cisplatin, Cladribine, Clomifene, Cyclophosphamide, Dacarbazine, Daclizumab, Dactinomycin, Dasatinib, Daunorubicin, Decitabine, Deslorelin, Dexrazoxane, Docetaxel, Doxifluridine, Doxorubicin, Droloxifene, Drostanolone, Edelfosine, Eflornithine, Emitefur, Epirubicin, Epitiostanol, Eptaplatin, Erbitux, Erlotinib, Estramustine, Etoposide, Exemestane, Fadrozole, Finasteride, Floxuridine, Flucytosine, Fludarabine, Fluorouracil, Flutamide, Formestane, Foscarnet, Fosfestrol, Fotemustine, Fulvestrant, Gefitinib, Genasense, Gemcitabine, Glivec, Goserelin, Gusperimus, Herceptin, Idarubicin, Idoxuridine, Ifosfamide, Imatinib, Improsulfan, Infliximab, Irinotecan, Ixabepilone, Lanreotide, Lapatinib, Letrozole, Leuprorelin, Lobaplatin, Lomustine, Luprolide, Melphalan, Mercaptopurine, Methotrexate, Meturedepa, Miboplatin, Mifepristone, Miltefosine, Mirimostim, Mitoguazone, Mitolactol, Mitomycin, Mitoxantrone, Mizoribine, Motexafin, Mylotarg, Nartograstim, Nebazumab, Nedaplatin, Nilutamide, Nimustine, Octreotide, Ormeloxifene, Oxaliplatin, Paclitaxel, Palivizumab, Panitumumab, Patupilone, Pazopanib, Pegaspargase, Pegfilgrastim, Pemetrexed, Pentetreotide, Pentostatin, Perfosfamide, Piposulfan, Pirarubicin, Plicamycin, Prednimustine, Procarbazine, Propagermanium, Prospidium Chloride, Raloxifen, Raltitrexed, Ranimustine, Ranpirnase, Rasburicase, Razoxane, Rituximab, Rifampicin, Ritrosulfan, Romurtide, Ruboxistaurin, Sargramostim, Satraplatin, Sirolimus, Sobuzoxane, Sorafenib, Spiromustine, Streptozocin, Sunitinib, Tamoxifen, Tasonermin, Tegafur, Temoporfin, Temozolomide, Teniposide, Testolactone, Thiotepa, Thymalfasin, Tiamiprine, Topotecan, Toremifene, Trail, Trastuzumab, Treosulfan, Triaziquone, Trimetrexate, Triptorelin, Trofosfamide, Uredepa, Valrubicin, Vatalanib, Vandetanib, Verteporfin, Vinblastine, Vincristine, Vindesine, Vinorelbine, Vorozole And Zevalin.

The amount of a vehicle of the invention comprising a therapeutic agent for administration to a patient to treat or prevent a disease condition will vary with the type of drug, and will comprise a therapeutically effective amount thereof. Dosages of therapeutic agents for treating various conditions are well known in the art. Note in this regard, for example, Goodman & Gilman's The Pharmacological Basis of Therapeutics, 2011, Twelfth Edition, McGraw-Hill, New York.

Diagnostic Agents

As stated above, a vehicle of the invention may also comprise a one or more different diagnostic agents, i.e., a diagnostic marker. In various embodiments, a vehicle of the invention comprises a combination of one or more diagnostic agents with one or more therapeutic agents.

In various embodiments, a vehicle of the invention comprises a fluorescent substance. For example, a fluorescent substance of the invention can be selected from, but not limited to fluorescein isothiosyanete (FITC), rhodamine, FAM, luminescent substances such as luminol, luciferin, lucigenin, or fluorescent drug compound (e.g., anthracycline class drugs such as daunorubicin) or any combination thereof.

In various embodiments, a vehicle of the invention comprises an electron dense substance. For example, an electron dense substance of the invention can be selected from, but not limited to ferritin, colloidal gold or colloidal superparamagnetic beads.

In various embodiments, a vehicle of the invention comprises a reporter molecule. For example, a reporter molecule of the invention can be selected from, but not limited to substituents that allow detection, either directly or indirectly, of compounds at low concentrations. Suitable reporter moieties include, but are not limited to, (1) enzymes, which produce a signal detectable, for example, by colorimetry, fluorescence or luminescence, such as horseradish peroxidase, alkaline phosphatase, beta-galactosidase or glucose-6-phosphate dehydrogenase; (2) chromophores, such as fluorescent, luminescent or dye compounds; (3) groups with an electron density which can be detected by electron microscopy or through their electrical property, such as by conductivity, amperometry, voltametry, or impedance measurements; and (4) groups which can be detected using optical methods, such as diffraction, surface plasma resonance or contact angle variation, or physical methods, such as atomic force spectroscopy, or the tunnel effect. Other suitable reporter moieties include, but are not limited to, biotin, digoxigenin, peptides, proteins, antibodies, glycoproteins, and sugars. Examples of specific binding moieties as diagnostic agents of the invention include antigen binding domains, growth factors, ligands, or oligonucleotides.

In various embodiments, a vehicle of the invention comprises a radioactive substance. For example, a radioactive substance of the invention can be selected from, but not limited to $^3$H, $^{14}$C, $^{32}$P, $^{33}$P, $^{35}$S, $^{123}$I, $^{125}$I, and $^{131}$I.

Methods of Treatment

As stated above, the method of treatment according to the invention administers a therapeutically effective amount of a vehicle, as described above, for the intracellular delivery of a therapeutic agent to an individual for the purpose of treating a disease. In various embodiments, the method of the invention treats hyperproliferative disorders. As understood herein, the term "hyperproliferative disorders" refers to disorders characterized by an abnormal or pathological proliferation of cells, including, for example, but not limited to tumors, cancers, neoplastic tissue and other premalignant and non-neoplastic or non-malignant hyperproliferative disorders. Examples of tumors, cancers, and neoplastic tissue that can be treated by the present invention include but are not limited to malignant disorders such as: breast cancers; osteosarcomas; angiosarcomas; fibrosarcomas and other sarcomas; leukemias; lymphomas; sinus tumors; ovarian, urethral, bladder, prostate and other genitourinary cancers; colon esophageal and stomach cancers and other gastrointestinal cancers; lung cancers; myelomas; pancreatic cancers; liver cancers; kidney cancers; endocrine cancers; skin cancers; and brain or central and peripheral nervous (CNS) system tumors, malignant or benign, including gliomas and neuroblastomas.

Examples of premalignant and non-neoplastic or non-malignant hyperproliferative disorders include but are not limited to myelodysplastic disorders; cervical carcinoma-in-situ; familial intestinal polyposes such as Gardner syndrome; oral leukoplakias; histiocytoses; keloids; hemangiomas; hyperproliferative arterial stenosis, inflammatory arthritis; hyperkeratoses and papulosquamous eruptions including arthritis. Also included are viral induced hyperproliferative diseases such as warts and EBV induced disease (i.e., infectious mononucleosis), scar formation, and the like. The methods of treatment disclosed herein may be employed with any subject known or suspected of carrying or at risk of developing a hyperproliferative disorder as defined herein.

As used herein, "treatment" of a hyperproliferative disorder refers to methods of killing, inhibiting or slowing the growth or increase in size of a body or population of hyperproliferative cells or tumor or cancerous growth, reducing hyperproliferative cell numbers, or preventing spread to other anatomic sites, as well as reducing the size of a hyperproliferative growth or numbers of hyperproliferative cells. "Treatment" also includes the diagnoses of hyperproliferative disorders by delivering diagnostic agents to target cells to allow the identification of target cells by detection methods that are known in the art. As used herein, "treatment" is not necessarily meant to imply cure or complete abolition of hyperproliferative growths. As used herein, a treatment effective amount of a therapeutic agent is an amount effective to result in the killing of hyperproliferative cells, the slowing of the rate of growth of hyperproliferative cells, the decrease in size of a body of hyperproliferative cells, or the reduction in number of hyperproliferative cells, and any combination thereof.

The method of treatment of the invention also includes combination therapies, including embodiments in which two or more vehicles of the invention respectively comprise different therapeutic agents or combinations of therapeutic agents, and are co-administered to a patient. In other embodiments, a vehicle of the invention, or combination of vehicles of the invention, can be administered in conjunction with another therapy. In addition to being co-administered with any of drug, including the drugs and classes of drugs provided above, a vehicle of the invention can also be administered in conjunction with other kinds of therapies, such as adjuvant and neoadjuvant therapies (e.g., any treatment given after primary therapy to increase the chance of long-term disease-free survival), biological therapies (e.g., immunotherapy, biotherapy, or biological response modifier therapy), bone marrow transplantation and peripheral blood stem cell transplantation, cancer vaccine therapy, cryosurgery, gene therapy, hormone therapy, laser therapy (e.g., high-intensity light to treat cancer), photodynamic therapy, radiation therapy, preventative mastectomy surgery, radiation therapy, or other targeted cancer therapies that are known to those in the art.

The term "treatment" also includes compositions and methods that are used to diagnose diseases by transporting a diagnostic marker into the intracellular compartment of a cell. More specifically, the vehicle of the invention may be detectably labeled by being linked to a detectable marker moiety such as a fluorescent label, an electron dense substance, a reporter moiety, a specific or nonspecific binding moiety, a radioactive, or other detectable moiety such as is known in the art, and that one of skill in the art deems to be appropriate for the particular disease that is to be detected and diagnosed by the method of the invention. The quantity of a vehicle of the invention that is administered for a diagnostic purpose should include an effective amount of the diagnostic label for the intended purpose. Such amounts can be determined empirically, and are also well known in the art.

Methods of Diagnosing

In various embodiments, the cystine component of the vehicle of the invention is labeled with a diagnostic marker, while in other embodiments the cargo component of the vehicle is labeled with the diagnostic marker. In still other embodiments the cystine and cargo components of the vehicle are labeled with the same or different diagnostic markers.

Examples of tissues to which the diagnostic methods of the invention can be applied include, but are not limited to: cancer cells, including, central nervous system tumors, breast cancer, liver cancer, lung, head and neck cancer, lymphomas, leukemias, multiple myeloma, bladder cancer, ovarian cancer, prostate cancer, renal tumors, sarcomas, colon and other gastrointestinal cancers, metastases, and melanomas. More specifically, the present invention can be applied to cancers such as sarcomas and carcinomas, e.g., fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, retinoblastoma; leukemias, e.g., acute lymphocytic leukemia and acute myelocytic leukemia (myeloblastic, promyelocytic, myelomonocytic, monocytic and erythroleukemia); chronic leukemia (chronic myelocytic (granulocytic) leukemia and chronic lymphocytic leukemia); and polycythemia vera, lymphoma (Hodgkin's disease and non-Hodgkin's disease), multiple myeloma, Waldenstrom's macroglobulinemia, and heavy chain disease.

Detection methods useful in practicing the present invention include, but are not limited to magnetic resonance, superconducting quantum interference device (squid), optical imaging, positron emission tomography, planar scintigraphy or single photon emission computed tomography (SPECT). Alternative methods of detection include gamma counting, scintillation counting, scanning radiograms, densitometry, fluorography, and visualization by electron microscopy. These detection methods can be employed during or after an effective time interval for diagnosis or imaging subsequent to administering a peptide complex of the present invention. Such effective time intervals are well known in the art, or can be determined by routine experimentation employing methods such as those disclosed herein.

Formulations

A vehicle of the invention, as described above, can be formulated as pharmaceutical dosage form and administered to a subject in need of treatment, for example a mammal, such as a human patient, in a variety of forms adapted to the chosen route of administration, for example, orally, enterally, mucosally, percutaneously, parenterally, intravenously, intramuscularly, subcutaneously, intracutaneously, intraarticularly, intrathecally and intraperitoneally by infusion or injection, as required, including continuous infusions or intermittent infusions with pumps available to those skilled in the art, or direct injection into the hyperproliferative tissue or cells.

The pharmaceutical compositions may be enclosed in hard or soft shell gelatin capsules, may be compressed into tablets, or may be incorporated directly with the food of the patient's diet. For oral therapeutic administration, the vehicle of the invention may be combined with one or more excipients and used in the form of ingestible tablets, buccal tablets, troches, capsules, elixirs, suspensions, syrups, wafers, and the like. The vehicle of the invention may be combined with a fine inert powdered carrier and inhaled by the subject or insufflated.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the vehicles of the invention may be incorporated into sustained-release preparations and devices.

Solutions of the vehicles of the invention can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations can contain a preservative to prevent the growth of microorganisms.

The pharmaceutical dosage forms suitable for injection or infusion can include sterile aqueous solutions or dispersions or sterile powders comprising the vehicles of the invention which are adapted for the extemporaneous preparation of sterile injectable or infusible solutions or dispersions. In all cases, the ultimate dosage form should be sterile, fluid and stable under the conditions of manufacture and storage. The liquid carrier can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by: i) the formation of liposomes if the cargo of the vehicle of the invention comprises a liposome; ii) by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions are prepared by incorporating the vehicles of the invention in the required amount in the appropriate solvent with various of the other ingredients enumerated above, as required, followed by filter sterilization. In the case of sterile powders for the preparation of sterile injectable solutions, the preferred methods of preparation are vacuum drying and freeze drying techniques, which yield a powder of the active ingredient plus any additional desired ingredient present in the previously sterile-filtered solutions.

For topical administration, the vehicles of the invention may be applied in pure form. However, it will generally be desirable to administer them to the skin as formulations, in combination with a dermatologically acceptable carrier, which may be a solid or a liquid. Useful solid carriers include finely divided solids such as talc, clay, microcrystalline cellulose, silica, alumina and the like. Other solid carriers include nontoxic polymeric nanoparticles or microparticles. Useful liquid carriers include water, alcohols or glycols or water/alcohol/glycol blends, in which the vehicles of the invention can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user. Examples of useful dermatological compositions which can be used to deliver the vehicles of the invention to the skin are known to the art; for example, see Jacquet et al. (U.S. Pat. No. 4,608,392), Geria (U.S. Pat. No. 4,992,478), Smith et al. (U.S. Pat. No. 4,559,157) and Wortzman (U.S. Pat. No. 4,820,508).

Useful dosages of vehicles of the invention can be determined by comparing their in vitro activity, and in vivo activity in animal models. Methods for the extrapolation of effective dosages in mice, and other animals, to humans are known to the art; for example, see U.S. Pat. No. 4,938,949. The amount of the vehicles of the invention required for use in treatment will vary depending on the particular therapeutic agent, the composition, if there is one, that comprises the therapeutic agent, the route of administration, the nature of the condition being treated and the age and condition of the patient, and will be ultimately at the discretion of the attendant physician or clinician.

A therapeutically effective dose can be determined empirically, by conventional procedures known to those of skill in the art. See, e.g., The Pharmacological Basis of Therapeutics, Goodman and Gilman, eds., Macmillan Publishing Co., New York. For example, an effective dose can be estimated initially either in cell culture assays or in suitable animal models. The animal model may also be used to determine the appropriate concentration ranges and routes of administration. Such information can then be used to determine useful doses and routes for administration in humans. A therapeutic dose can also be selected by analogy to dosages for comparable therapeutic agents.

The particular mode of administration and the dosage regimen will be selected by the attending clinician, taking into account the particulars of the case (e.g., the subject, the disease, the disease state involved, and whether the treatment is prophylactic). Treatment may involve daily or multi-daily doses of compound(s) over a period of a few days to months, or even years.

EXAMPLES

Example 1

Preparation of Daunorubicin (DNR)-Loaded Liposomes

Liposomes were prepared by the thin film hydration method from a lipid mixture of dipalmitoylphosphatidylcholine (DPPC), dipalmitoylphosphatidylglycerol (DPPG) and cholesterol at a ratio 12:1:5 and a total combined weight of 20 mg. The lipid mixture was dissolved in 5 to 8 ml of chloroform, and then rotary-evaporated in a round bottomed flask under vacuum conditions at room temperature to yield a thin lipid film. To the resulting lipid film, was added 2 to 3 ml of a buffered solution of 20 mM sodium borate and 0.15 M NaCl with a pH of 8.4. The buffered solution was allowed to stand with the lipid film for 15 minutes. The buffered solution-lipid film mixture was then vortexed, homogenized by sonication for 2 minutes, and then extruded 10 times with a mini extruder through a polycarbonate membrane with a 100 nm nuclepore Whatman™ filter (GE Healthcare). After the extrusion procedure was performed, the liposomal solution was frozen at −80° C. and lyophilized. The freeze dried empty liposomes were then stored at −20° C. until use.

Empty liposomes were loaded with DNR by adding 11.56 mg of daunorubicin hydrochloride that had been dissolved in 500 μl of sterile PBS to the freeze-dried liposomal powder, incubating the DNR-liposome mixture at 37° C. for 1 hour, then diluting the mixture in sterile PBS up to a total volume of 2 ml, and incubating an additional hour at 37° C. The final DNR concentration in the liposome-DNR mixture was 10 mM. The liposomal suspension was mixed by pipetting to disperse the liposomes, and subsequently centrifuged at 13,000 rpm for 40 minutes in order to remove the unencapsulated DNR. After the centrifugation step, the supernatant was then removed and 2 ml of sterile PBS was added to the pellet, and the pellet was resuspended by pipetting.

The particle sizes of the DNR-liposomes were measured by using a Nicomp™ 380 submicron particle sizer (Particle Sizing Systems, Santa Barbara, Calif.). To prepare the liposomes for size measuring, 1 mg of Liposomal DNR were sonicated in 1 ml PBS for about 1-2 minutes and then diluted with PBS to a volume of 2 ml. The PBS-suspended liposomes were then measured by the Nicomp™ particle sizer in accordance with the manufacturer's instructions.

Figure 4:
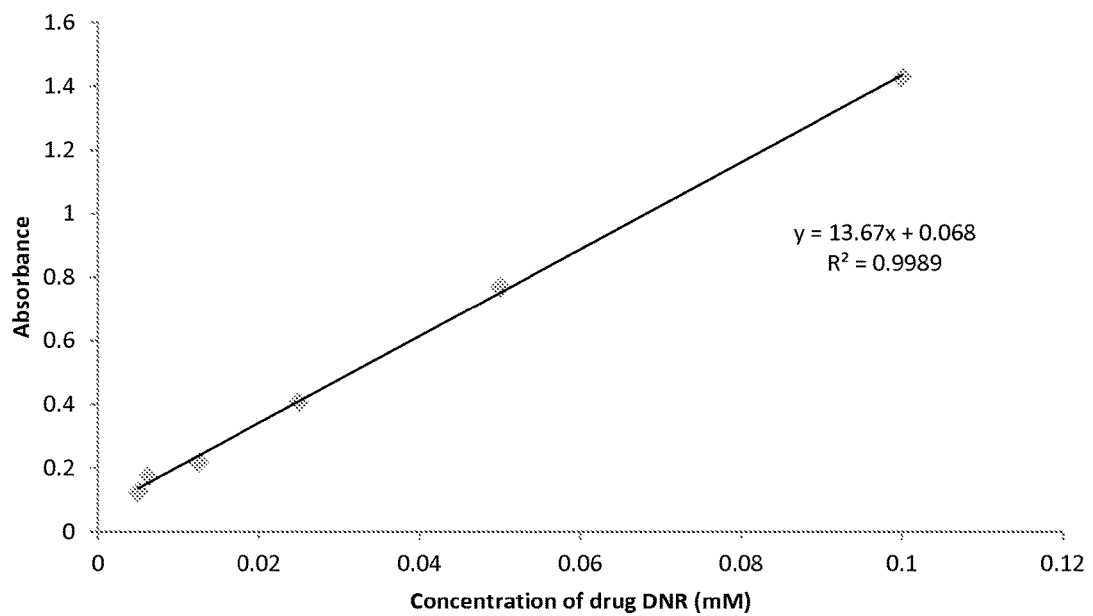
FIG. 4 shows a standard curve (absorbance versus DNR concentration) of DNR for A549 cells.

The amount of DNR in a particular preparation of Liposomal DNR was assessed by measuring the DNR in the liposomes directly by using UV-VIS spectrophotometer at a wavelength of 455 nm (UV Shimandzu), and comparing absorbance to the standard curve of absorbance versus DNR concentration that is shown in FIG. 4. Based on the amount of DNR present in a DNR-liposome preparation, encapsulation efficiency was then calculated according to the following equation: Encapsulation Efficiency (%)=$F_t/F_i \times 100$, wherein $F_t$ is the concentration of DNR in the liposomes after dissolution in an organic solvent mixture consisting of chloroform: methanol: water (2:1:0.05) and $F_i$ is the initial concentration of the DNR in the media before encapsulation. Generally, encapsulation efficiency for the Liposomal DNR was 20% to 25%.

Example 2

Preparation of Cystine Liposomal DNR

Empty liposomes were prepared as described in Example 1 through the extrusion step. After extruding the liposomes, 4 ml of a 0.6 M sodium periodate solution was added to the liposomal suspension, and the mixture was left to react for 30 min in dark. This step oxidizes the diol moieties on the liposomal surface. After the sodium periodate reaction step, the sodium periodate liposome mixture was loaded into dialysis tubing (M.W 14,000 KD, Spectrum labs), and dialyzed against water for 12 hours at 4° C. by using to remove any unreacted sodium periodate. Cystine molecules were conjugated to the surface of the periodate-oxidized liposomes by a reductive amination reaction that was performed as follows. First, 60 mg of cystine was dissolved in the buffered solution that is described in Example 1 (20 mM Sodium Borate and 0.15 M NaCl at pH 8.4) to a concentration of 10mg/ml. The dialyzed liposomal suspension and the cystine solution were mixed and left to react to form a schiff-base. Then, 10 μl of 2M cyanoboronhydride solution was added to the liposome suspension-cystine solution mixture for each ml of the mixture, and the total mixture was left to react at room temperature overnight, and subsequently dialyzed against water for 12 hours at 4° (by once again using 14,000 KD M.W dialysis tubing (Spectrum labs) to remove any unconjugated cystine. The dialyzed liposomal suspension was frozen at −80° C. and freeze dried in lyophilizer. The freeze dried empty cystine conjugated liposomes were stored at −20° C. and reconstituted before use. DNR-loading steps of the cystine-liposomes, as well as particle sizing and DNR-loading efficiency analyses, were performed as described in Example 1 for DNR loading of liposomes. Generally, encapsulation efficiency for the cystine liposomal DNR was 15% to 20%.

Example 3

Cellular Uptake of DNR Following the Addition of Either Free DNR, Liposomal DNR, or Cystine Liposomal DNR Fluorescence Activated Cell Sorting (FACS) and fluorescence microscopy were used to detect DNR, a fluorescent compound, in A549 human lung cancer cell line cells following treatment with either free DNR, Liposomal DNR, or cystine liposomal DNR. A549 cells highly expresses the $x_c^-$ transporter, and thus, are well suited for cystine-mediated uptake studies. (Gatti & Zunino, 2005). A549 cells were cultured in RPMI 1640 medium that was supplemented with 10% heat inactivated FBS and 1% antibiotic (penicillin/streptomycin) in a 25 cm$^2$ tissue culture flask at 37° C. in a humidified atmosphere of 5% carbon dioxide. The A549 cells were cultured as a monolayer and passaged twice a week in accordance with standard tissue culture procedures until the cells were used for experiments.

For the DNR uptake experiments, the A549 cells cultured in 25 cm$^2$ tissue culture flasks, as described above, were trypsinized, washed, and re-seeded into 6-well tissue culture plates by placing 3×10$^5$ cells suspended in 2 ml of RPMI 1640 medium that was supplemented with 10% heat inactivated FBS and 1% antibiotic in each well. After allowing the cells to rest for 24 hours under the culture conditions described above, the cells were treated in the following manners. Triplicate wells were treated by adding to the media in the wells, the following formulations of DNR: 1)

Cystine liposomal DNR containing 10 µM of DNR; 2) Cystine liposomal DNR containing 5 µM of DNR; 3) Liposomal DNR containing 10 µM of DNR; 4) Cystine liposomal DNR containing 5 µM of DNR; 5) 10 µM of free DNR; and 6) 5 µM of free DNR. The cells were incubated with the DNR formulations for 5 hours at 37° C. in a humidified atmosphere of 5% carbon dioxide. DNR uptake by the cells was then determined by FACS and fluorescence microscopy methods.

FACS Analysis.

Figure 5A:
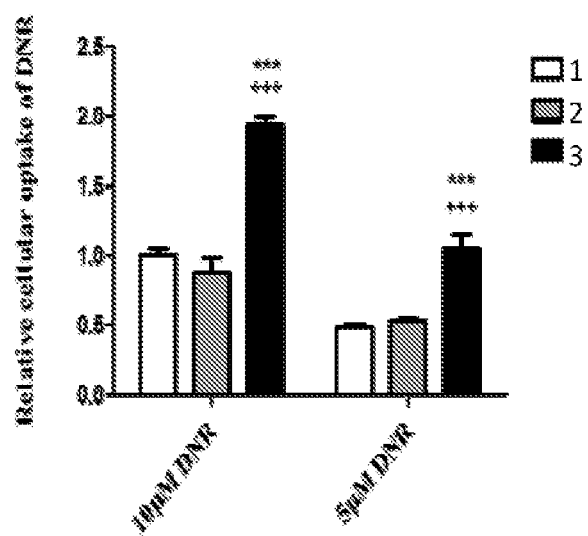
FIG. 5A shows a bar graph representation of the relative cellular uptake of 10 μm and 5 μm of DNR in the form of either: (1) free DNR; (2) liposomal DNR; and (3) cystine-liposomal DNR by A549 cells based on fluorescence intensity as measured by flow cytometry analysis. The graph represents the mean fluorescence intensities (MFI) of the different represented DNR formulations based on flow cytometry data. Cellular DNR uptake is expressed as the mean fluorescence intensities of the different represented DNR formulations relative to 10 μM free DNR. Mean and S.E.M are shown (***p<0.001 for cystine-liposomal DNR vs. free DNR for the 5 μM and 10 μM concentrations, n=3; +++p<0.001 for cystine-liposomal DNR vs. liposomal DNR for the 5 μM and 10 μM concentrations.)
Figure 5B:
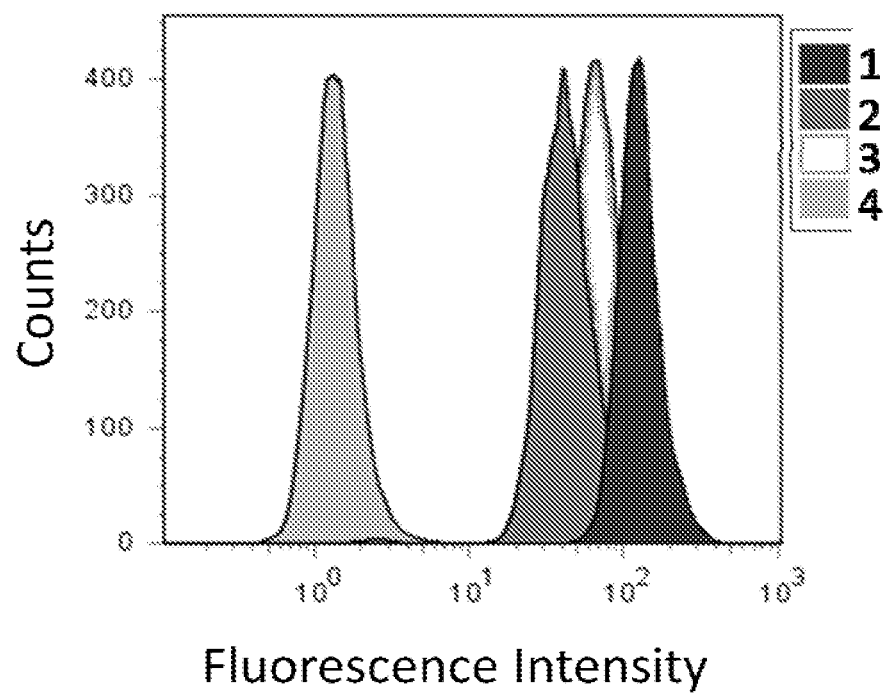
FIG. 5B shows a histogram of DNR uptake by A549 cells that were treated with either: (1) cystine-liposomal DNR; (2) non-cystine-liposomal DNR; (3) free DNR; or (4) nothing. All DNR formulations contained 10 μm of DNR. (n=3). Cellular uptake of DNR correlates to fluorescence intensity.
Figure 5C:
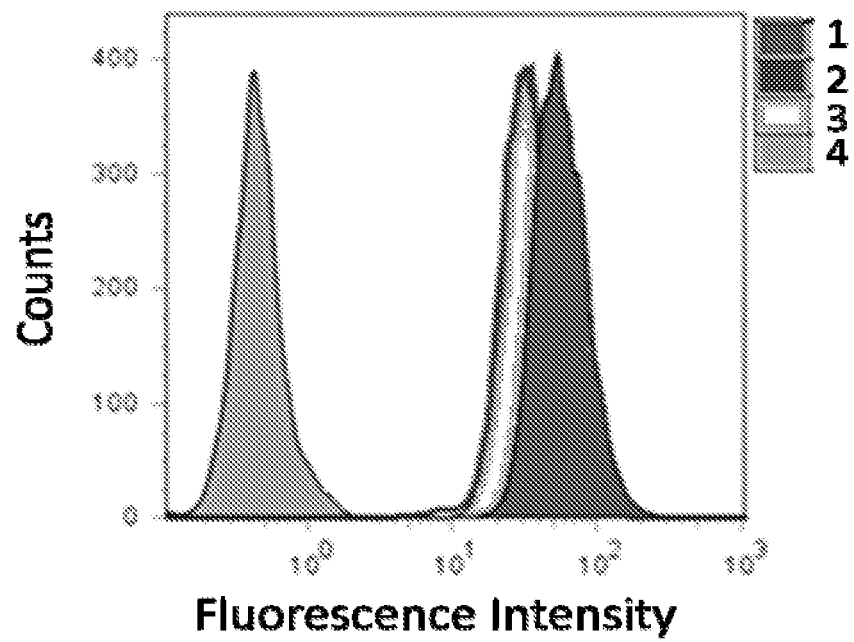
FIG. 5C shows a histogram of DNR uptake by A549 cells that were treated with either: (1) cystine-liposomal DNR; (2) free DNR; (3) non-cystine-liposomal DNR; or (4) nothing. All DNR formulations contained 5 μm of DNR. (n=3). Cellular uptake of DNR correlates to fluorescence intensity.

At the end of the treatment of A549 cells with free DNR, Liposomal DNR, or Cystine liposomal DNR, the media from the wells was aspirated and the cells were washed with sterile PBS solution. To detach the cells from the flask, 100 µl to 200 µl of trypsin (0.25% w/v) was added to the cells, and the cells were incubated in the trypsin solution for approximately 1 to 3 minutes, after which 1 ml of growth medium was added to each well to stop the trypsin activity. The resulting cell suspension in each well was centrifuged at 2000 rpm for 3 minutes at 4° C. The supernatant was aspirated, and the cell pellets were resuspended in 500 µl of sterile ice cold PBS solution. The cell suspensions were then transferred to sterile polystyrene tubes. Cellular uptake of DNR was quantified by detecting the fluorescent signal at the FL3 channel. Mean fluorescence intensity values were also determined. A549 cells that had not received DNR or liposomes were used as a negative control. FIG. 5A shows the mean fluorescence intensities (MFI) of the different represented DNR formulations. Cellular DNR uptake is expressed as the mean fluorescence intensities of the different represented DNR formulations relative to 10 µM free DNR. Mean and S.E.M are shown (***$p<0.001$ for cystine-liposomal DNR vs. free DNR for the 5 µM and 10 µM concentrations, n=3; +++$p<0.001$ for cystine-liposomal DNR vs. liposomal DNR for the 5 µM and 10 µM concentrations). The number of cell counts that correlate to the fluorescence intensities that were used to calculate the MFI shown in FIG. 5A are reported in histogram that is shown in FIG. 5B and FIG. 5C for the 10 µM and 5 µM amounts of DNR, respectively. Statistical comparisons were determined with two-way ANNOVA and one-way ANOVA and the pairwise analysis was done using Bonferonni's and Tukey's post hoc test respectively. All calculations were using Graphpad Prism™ 5 (GraphPad Software, Inc., San Diego, Calif.). Differences with a P value less than 0.05 were considered to be statistically significant.

Fluorescence Microscopy. Intracellular DNR in A549 cells was observed by fluorescence microscopy analysis at the end of the treatment of A549 cells with free DNR, Liposomal DNR, or Cystine liposomal DNR. Cells were observed with a fluorescence microscope under bright light or fluorescence with green filter. For the fluorescence imaging, the images of cells stained with DNR, which is a natural fluorescent drug are captured. DNR fluorescence was analyzed by using Nikon Eclipse™ Ti series inverted microscope (Nikon Instruments, Inc. Melville, N.Y.), and images were captured by using NIS Elements™ software (Nikon Instruments, Inc. Melville, N.Y.).

Figure 6A:
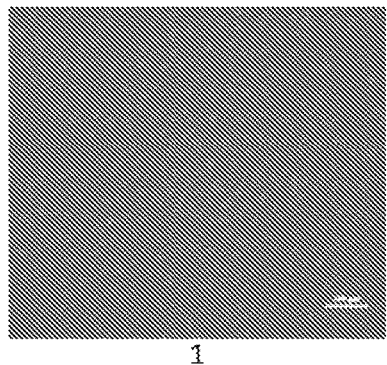
FIG. 6A shows fluorescence microscopy images of A549 cells incubated for six hours at 37° C. with either: (1) 10 μM DNR; (2) a 10 μM DNR equivalent amount of cystine liposomal DNR; (3) a 10 μM DNR equivalent amount of liposomal DNR; or (4) a 10 μM DNR equivalent amount of cystine liposomal DNR in the presence of glutamate.
Figure 6A:
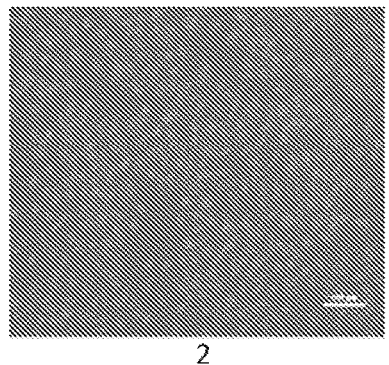
Figure 6A:
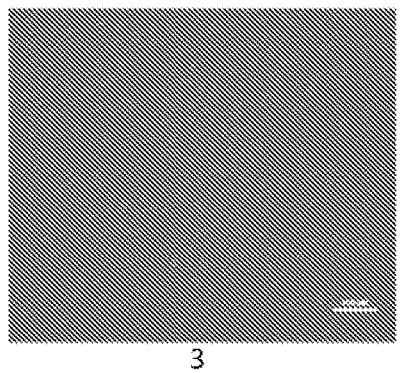
Figure 6A:
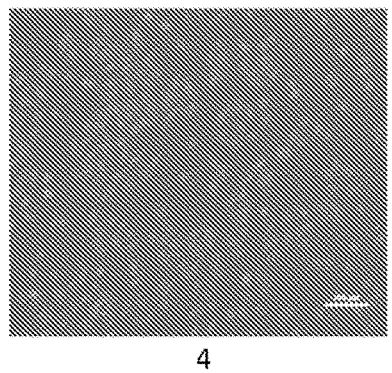
Figure 6B:
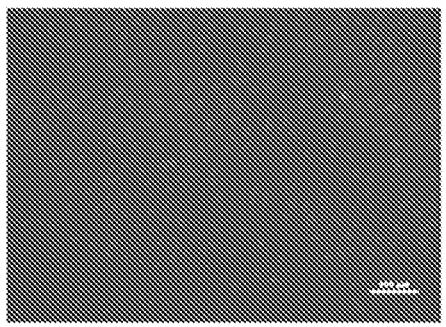
FIG. 6B shows fluorescence microscopy images of A549 cells incubated for six hours at 37° C. with either: (1) 5 μM DNR; (2) a 5 μM DNR equivalent amount of cystine liposomal DNR; (3) a 5 μM DNR equivalent amount of liposomal DNR; or (4) a 5 μM DNR equivalent amount of cystine liposomal DNR in the presence of glutamate.
Figure 6B:
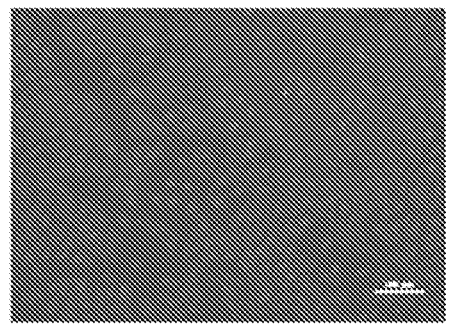
Figure 6B:
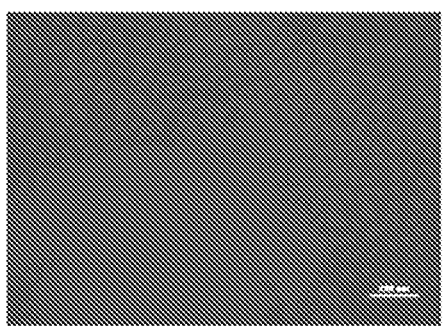
Figure 6B:
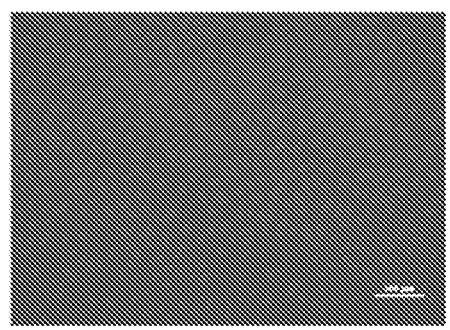

Consistent with the FACS results, above, analysis, the fluorescence microscopic images showing relatively high fluorescence in cells that were treated with Cystine liposomal DNR versus those cells treated with either free DNR or Liposomal DNR. Also, the fluorescence of liposomal DNR did not show any difference compared to the fluorescence of free DNR. The fluorescence microscopic and the flow cytometry data are in consistent which shows the enhanced cellular uptake of the cystine liposomal DNR compared to the liposomal DNR and the free DNR. See FIG. 6A and FIG. 6B for fluorescence microscopy images of cells that were treated with 10 µM and 5 µM DNR, respectively, in the forms of free DNR, Liposomal DNR, or cystine liposomal DNR.

Example 4

Figure 7A:
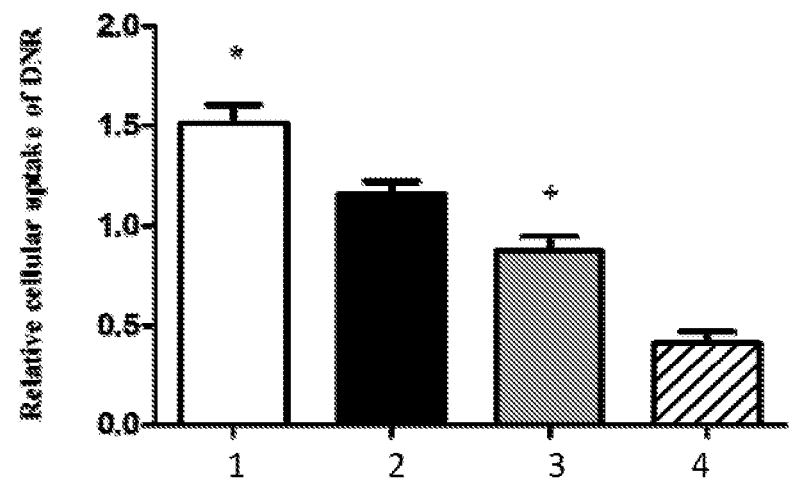
FIG. 7A shows a bar graph of the effect of glutamate (5 mM) on DNR uptake by cells treated with a cystine-liposomal DNR formulation that contained either 5 μm or 10 μm doses of DNR. The graph represents the mean fluorescence intensities (MFI) of the different represented DNR formulations based on flow cytometry data. Cellular DNR uptake is expressed as the mean fluorescence intensities of the different represented DNR formulations relative to 10 μM free DNR. Mean and S.E.M are shown (*$p<0.05$ for cystine-liposomal DNR vs. liposomal DNR are shown for the 5 μM and 10 μM concentrations, n=3). Bar (1) shows DNR uptake following the addition of 10 μm amount of DNR in the form of cystine-liposomal DNR. Bar (2) shows DNR uptake in the presence of glutamate following the addition of 10 μm amount of DNR in the form of cystine-liposomal DNR. Bar (3) shows DNR uptake following the addition of 5 μm amount of DNR in the form of cystine-liposomal DNR. Bar (4) shows DNR uptake in the presence of glutamate following the addition of 5 μm amount of DNR in the form of cystine-liposomal DNR.
Figure 7B:
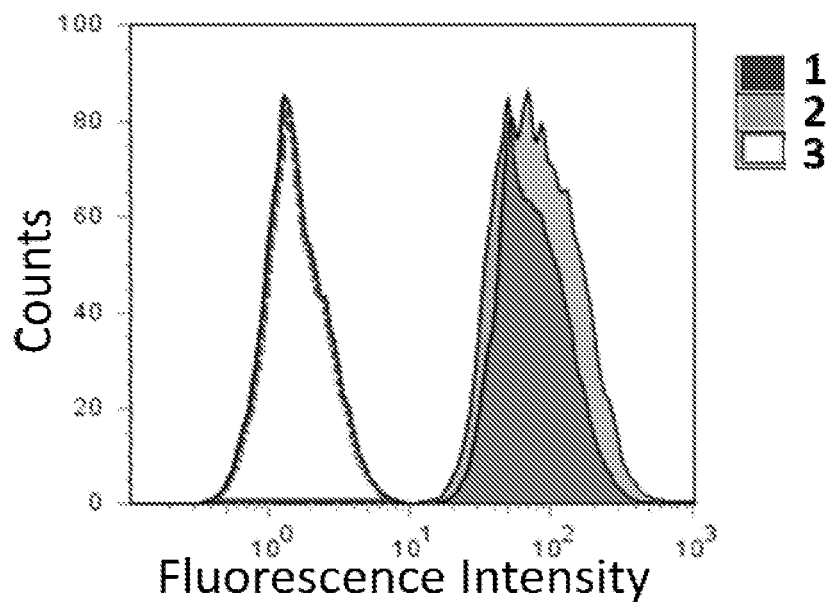
FIG. 7B shows a histogram of the effect of glutamate on DNR uptake by cells treated with a cystine-liposomal DNR formulation that contained a 10 μm dose of DNR. Cell counts versus fluorescence intensities are shown for A549 cells that were treated with either: (1) cystine-liposomal DNR; (2) cystine-liposomal DNR and glutamate; and (3) nothing. (n=3).
Figure 7C:
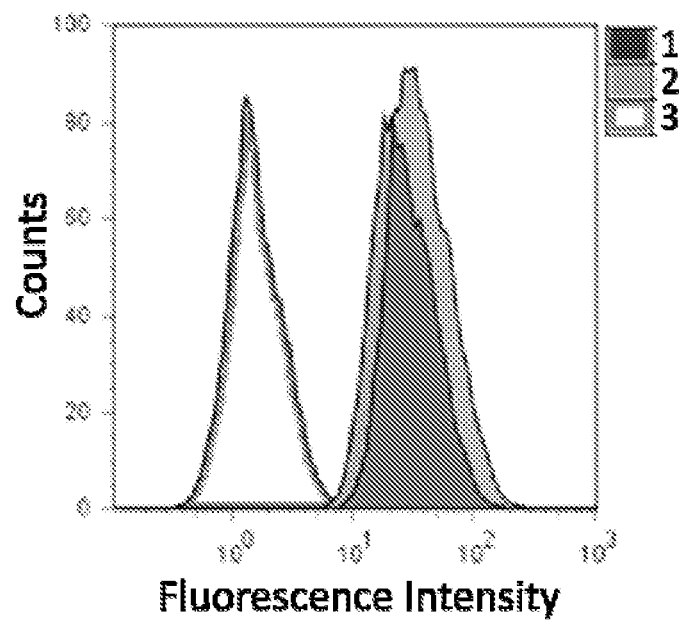
FIG. 7C shows a histogram of the effect of glutamate on DNR uptake by cells treated with a cystine-liposomal DNR formulation that contained a 5 μm dose of DNR. Cell counts versus fluorescence intensities are shown for A549 cells that were treated with either: (1) cystine-liposomal DNR; (2) cystine-liposomal DNR and glutamate; and (3) nothing. All DNR formulations contained 5 μm of DNR. (n=3).

Pretreatment of Cells with Glutamate Inhibits Cystine-Mediated Cellular Uptake of DNR from Cystine Liposomal DNR In order to demonstrate the potential role that the $x_c^-$ transporter plays in the uptake of DNR from cystine liposomal DNR, A549 cells were pretreated with glutamate, a specific inhibitor of cystine uptake through the $x_c^-$ transporter, prior to introducing cystine liposomal DNR. To perform these uptake inhibition studies, A549 cells were plated in triplicate wells of 6-well plates, and treated with Cystine liposomal DNR that contained either 10 µm or 5 µm amounts of DNR exactly as described above in Example 3, except that the cells were pre-treated with a 5 mM concentration of glutamate (Sigma-Aldrich) for 30 minutes prior to the introduction of the DNR formulations. FACS analysis of DNR uptake was performed according to the protocol described in Example 3. Results from the FACS analysis showed that pre-treatment with 5 mM glutamate reduced DNR cellular uptake by about a 1.3 fold and 2.1 fold in cells that were treated with 10 µM DNR and 5 µM DNR, respectively, cystine liposomal DNR. See FIG. 7A, showing the MFI of DNR fluorescence in glutamate untreated and treated 10 µM and 5 µM cystine liposomal DNR, wherein cellular DNR uptake is expressed as the MFI relative to the fluorescent intensity based on treatment of A549 cells with 10 µM free DNR. The relationship between cell counts versus fluorescence intensities in these glutamate treatment studies are shown for the A549 cells that were treated with cystine liposomal DNR containing 10 µM and 5 µM DNR in FIGS. 7B and 7C, respectively.

Example 5

Cold Temperature Effect on DNR Cellular Uptake from Cystine Liposomal DNR

Figure 8A:
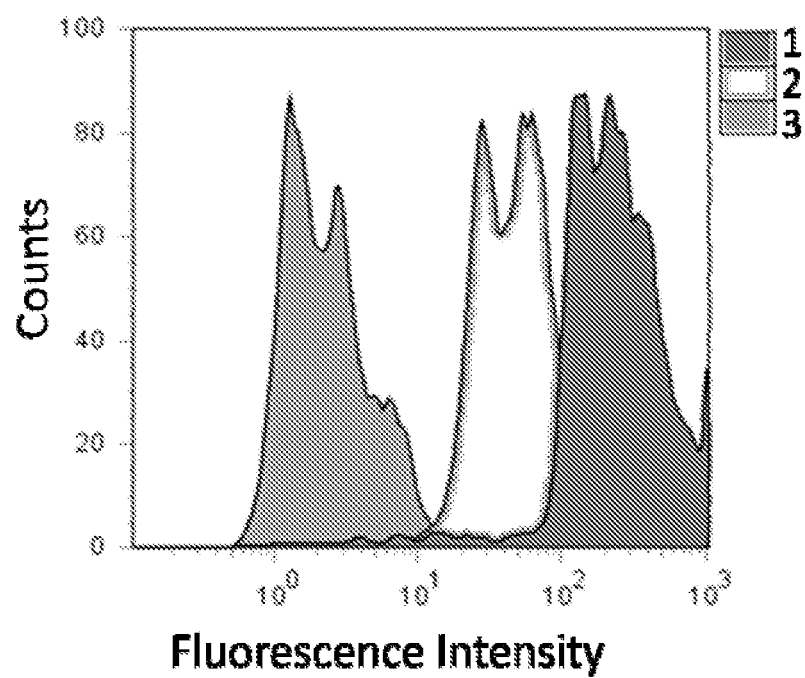
FIG. 8A shows a histogram of the effect of cold temperature on DNR uptake by cells treated with a cystine-liposomal DNR formulation that contained a 10 μm dose of DNR. Cell counts versus fluorescence intensities are shown for A549 cells that were treated with either: (1) cystine-liposomal DNR; (2) cystine-liposomal DNR under cold conditions (4° C.); and (3) nothing. All DNR formulations contained 10 μm of DNR. (n=3).
Figure 8B:
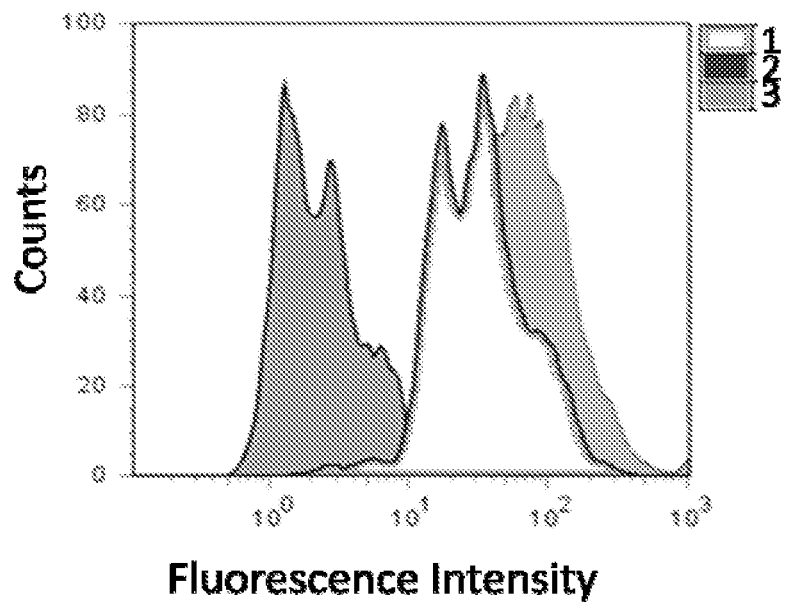
FIG. 8B shows a histogram of the effect of cold temperature on DNR uptake by cells treated with a cystine-liposomal DNR formulation that contained a 5 μm dose of DNR. Cell counts versus fluorescence intensities are shown for A549 cells that were treated with either: (1) cystine-liposomal DNR; (2) cystine-liposomal DNR under cold conditions (4° C.); and (3) nothing. All DNR formulations contained 5 μm of DNR. (n=3).

The influence of cold temperature on the cellular uptake of DNR from cystine liposomal DNR was examined in order to determine whether the uptake of cystine liposomal DNR is an energy dependent endocytotic process. To perform these temperature studies, A549 cells were plated in triplicate wells of 6-well plates, and treated with cystine liposomal DNR that contained either 10 µm or 5 µm amounts of DNR exactly as described above in Example 3, except that for those cells subjected to cold temperatures, the 5 hour incubation with the DNR-loaded cystine liposome formulations was performed at 4° C. FACS analysis of DNR uptake was performed according to the protocol described in Example 3. As shown for A549 cells that were treated with 10 µM and 5 µM DNR-loaded cystine liposome formulations in FIGS. 8A and 8B, respectfully, cellular intake of DNR was reduced under the 4° C. conditions versus under the 37° C. conditions. Therefore, these data suggest that the cellular uptake of DNR from Cystine liposomal DNR is an energy dependent process.

Example 6

The Effect of Inhibiting Caveolae Mediated Endocytosis on DNR Cellular Uptake from Cystine Liposomal DNR In view of the cold temperature studies described in Example 5 that suggested uptake of DNR from cystine liposomal DNR involves endocytosis, subsequent DNR uptake studies were performed that tested the ability of certain inhibitors of particular mechanisms of endocytosis to inhibit DNR uptake from cystine liposomal DNR. The first of these studies sought to determine whether the DNR uptake mechanism from cystine liposomal DNR involved caveolae mediated endocytosis. More particularly, cytochalasin D, a specific uptake inhibitor of caveolae mediated endocytosis was used to pre-treat the A549 cells prior to culturing the cells with cystine liposomal DNR. To perform these uptake inhibition studies, A549 cells were plated in triplicate wells of 6-well plates, and treated with cystine liposomal DNR that contained either 10 μm or 5 μm amounts of DNR exactly as described above in Example 3, except that the cells were pre-treated with a 100 μM concentration of cytochalasin D (Sigma-Aldrich) for 30 minutes prior to the introduction of the DNR formulations. FACS analysis of DNR uptake was performed according to the protocol described in Example 3.

Figure 9A:
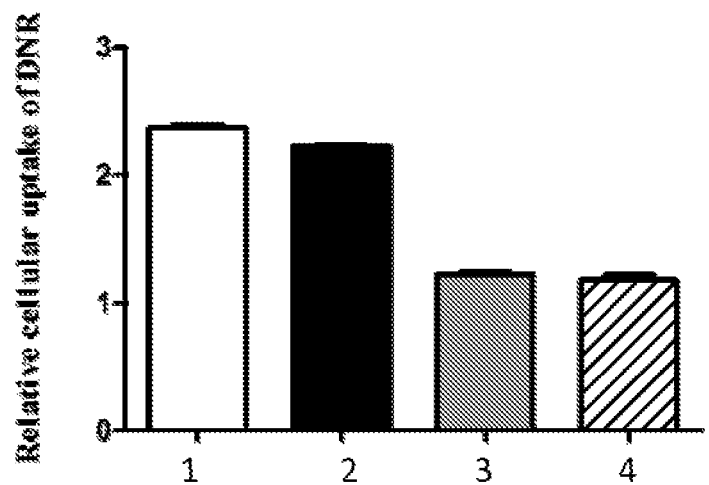
FIG. 9A shows a bar graph of the effect of cytochalasin (100 μM) on DNR uptake by cells treated with cystine-liposomal DNR formulations that contained either 5 μm or 10 μm doses of DNR. The graph represents the mean fluorescence intensities (MFI) of the different represented DNR formulations based on flow cytometry data. Cellular DNR uptake is expressed as the mean fluorescence intensities of the different represented DNR formulations relative to 10 μM free DNR. Mean and S.E.M are shown. Bar (1) shows DNR uptake following the addition of 10 μm amount of DNR in the form of cystine-liposomal DNR. Bar (2) shows DNR uptake in the presence of cytochalasin following the addition of 10 μm amount of DNR in the form of cystine-liposomal DNR. Bar (3) shows DNR uptake following the addition of 5 μm amount of DNR in the form of cystine-liposomal DNR. Bar (4) shows DNR uptake in the presence of cytochalasin following the addition of 5 μm amount of DNR in the form of cystine-liposomal DNR.
Figure 9B:
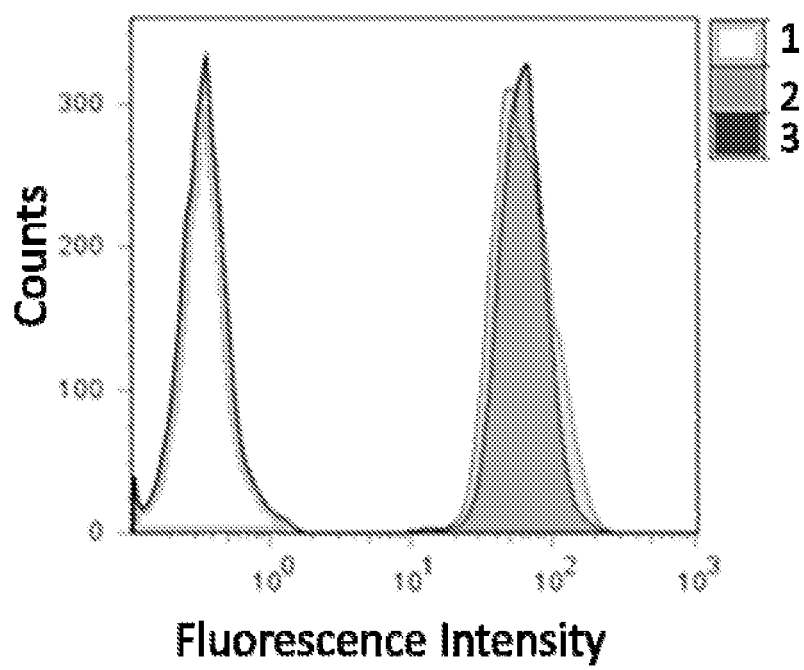
FIG. 9B shows a histogram of the effect of cytochalasin on DNR uptake by cells treated with a cystine-liposomal DNR formulation that contained a 10 μm dose of DNR. Cell counts versus fluorescence intensities are shown for A549 cells that were treated with either: (1) nothing; (2) cystine-liposomal DNR; and (3) cystine-liposomal DNR and cytochalasin. (n=3).
Figure 9C:
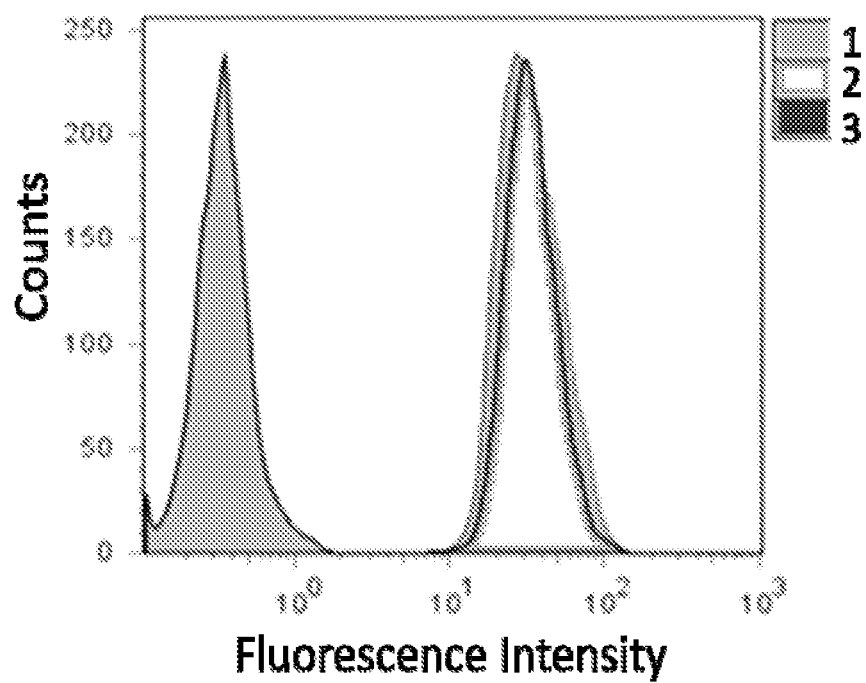
FIG. 9C shows a histogram of the effect of cytochalasin on DNR uptake by cells treated with a cystine-liposomal DNR formulation that contained a 5 μm dose of DNR. Cell counts versus fluorescence intensities are shown for A549 cells that were treated with either: (1) nothing; (2) cystine-liposomal DNR and cytochalasin; or (3) cystine-liposomal DNR. (n=3).

Results from the FACS analysis showed that pre-treatment with 100 μM cytochalasin D did not significantly reduce DNR cellular uptake by cells that were treated with 10 μM DNR or 5 μM Cystine liposomal DNR. See FIG. 9A, showing the MFI of DNR fluorescence in cytochalasin D untreated and treated A549 cells that had received either 10 μM or 5 μM Cystine liposomal DNR. More particularly, one way ANOVA shows relative mean fluorescence intensity of DNR shows significant difference of treatments (F3, 8=588.73; P<0.001). Further analysis of the data using Tukey's post-hoc test in FIG. 9A shows no significant difference in relative mean fluorescence intensity of cystine liposomal DNR treated with cytochalasin compared to non-treated cystine liposomal DNR for both concentrations (10 μM and 5 μM). There were also no any difference in the cellular uptake of DNR from cystine liposomal DNR, administered alone, as compared to the uptake of DNR from cystine liposomal DNR by cells that were pre-treated with cytochalasin D, irrespective of whether 10 μM or 5 μM amounts of DNR were added. See FIGS. 9B and 9C.

Example 7

The Effect of Inhibiting Chalathrin-Mediated Endocytosis on DNR Cellular Uptake from Cystine Liposomal DNR Further to the discussion in Example 6 concerning identifying endocytotic mechanisms that may be involved in the cellular uptake of DNR from DNR-loaded cytosine liposomes, chlorpromazine, a specific inhibitor of clathrin-mediated endocytosis, was used in the following DNR uptake studies to determine whether the DNR uptake mechanism from cystine liposomal DNR involved chlathrin-mediated endocytosis. These studies were performed by plating A549 cells in triplicate wells of 6-well plates, and treated with Cystine liposomal DNR that contained either 10 μm or 5 μm amounts of DNR exactly as described above in Example 3, except that the cells were pre-treated with a 10 μg/ml concentration of chlorpromazine (Sigma-Aldrich) for 30 minutes prior to the introduction of the DNR formulations. FACS analysis of DNR uptake was performed according to the protocol described in Example 3.

Figure 10A:
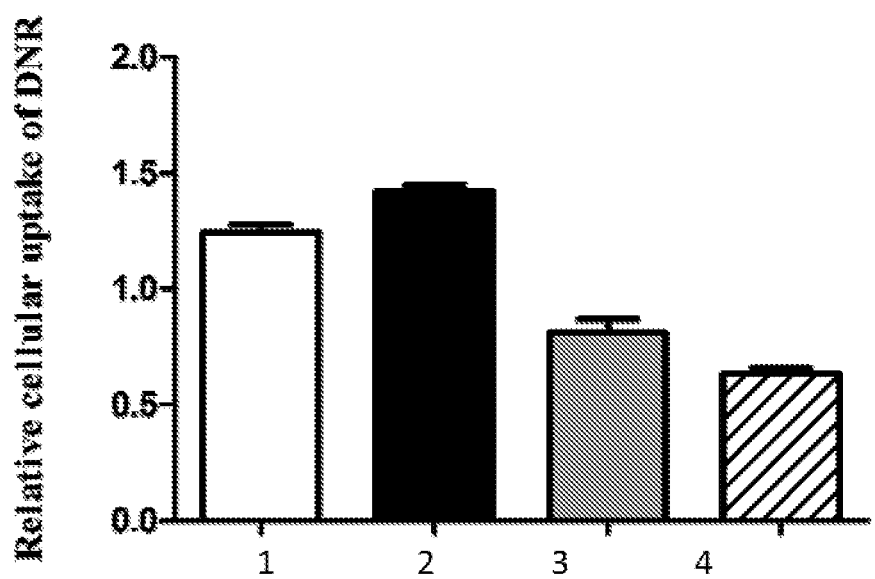
FIG. 10A shows a bar graph of the effect of chlorpromazine (10 μg/ml) on DNR uptake by cells treated with cystine-liposomal DNR formulations that contained either 5 μm or 10 μm doses of DNR. The graph represents the mean fluorescence intensities (MFI) of the different represented DNR formulations based on flow cytometry data. Cellular DNR uptake is expressed as the mean fluorescence intensities of the different represented DNR formulations relative to 10 μM free DNR. Mean and S.E.M are shown. Bar (1) shows DNR uptake following the addition of 10 μm amount of DNR in the form of cystine-liposomal DNR. Bar (2) shows DNR uptake in the presence of chlorpromazine following the addition of 10 μm amount of DNR in the form of cystine-liposomal DNR. Bar (3) shows DNR uptake following the addition of 5 μm amount of DNR in the form of cystine-liposomal DNR. Bar (4) shows DNR uptake in the presence of chlorpromazine following the addition of 5 μm amount of DNR in the form of cystine-liposomal DNR.
Figure 10B:
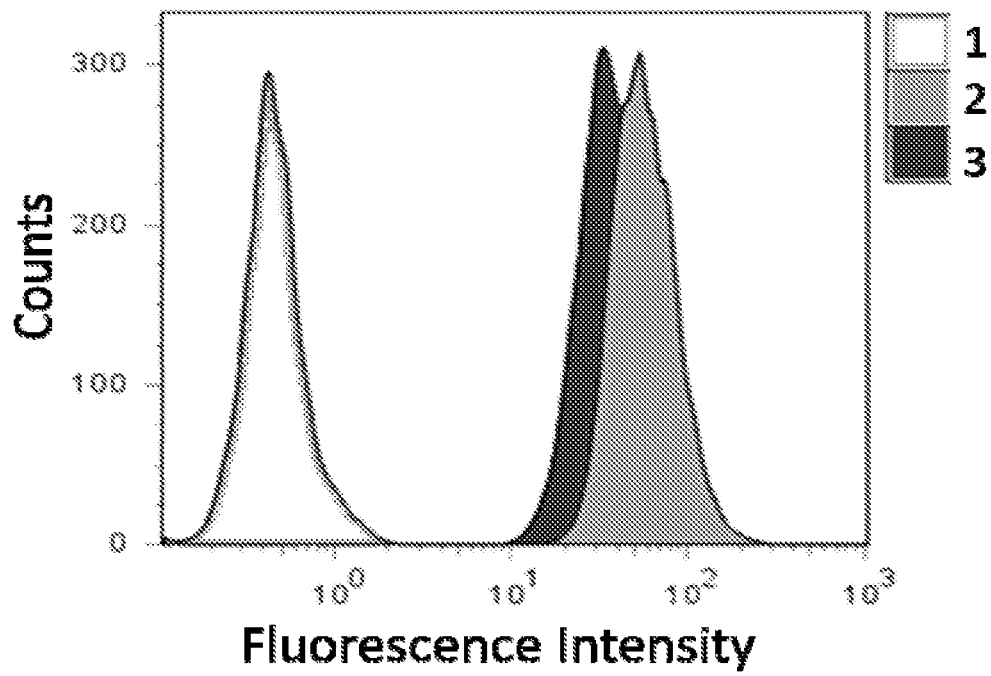
FIG. 10B shows a histogram of the effect of chlorpromazine on DNR uptake by cells treated with a cystine-liposomal DNR formulation that contained a 5 μm dose of DNR. Cell counts versus fluorescence intensities are shown for A549 cells that were treated with either: (1) nothing; (2) cystine-liposomal DNR; and (3) cystine-liposomal DNR and chlorpromazine. (n=3).
Figure 10C:
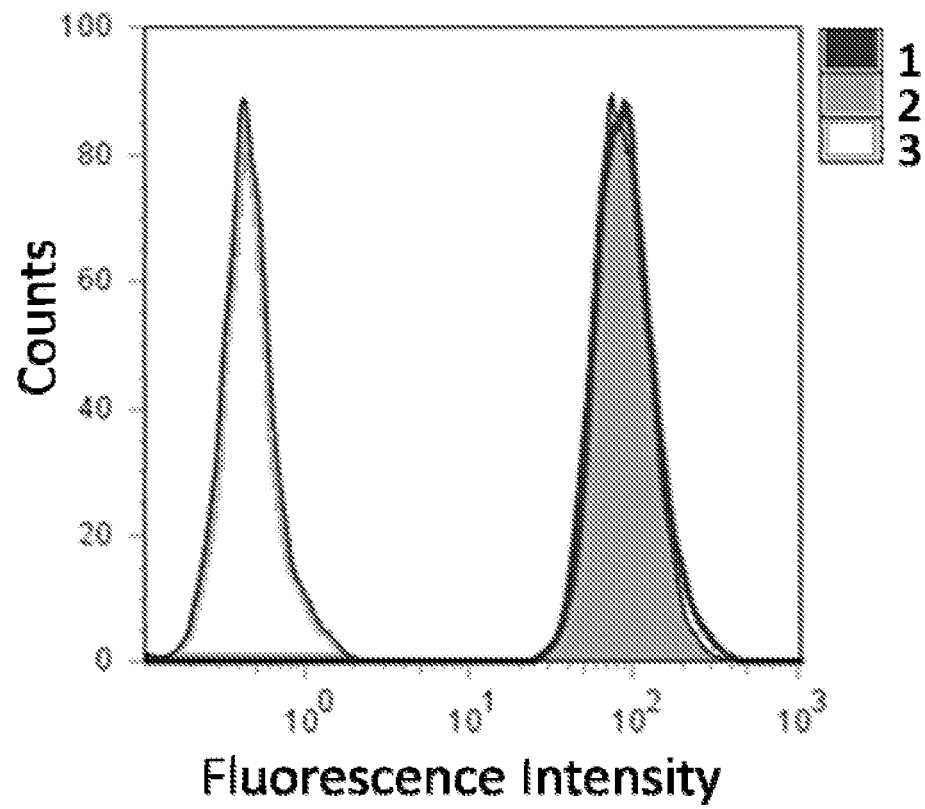
FIG. 10C shows a histogram of the effect of chlorpromazine on DNR uptake by cells treated with a cystine-liposomal DNR formulation that contained a 10 μm dose of DNR. Cell counts versus fluorescence intensities are shown for A549 cells that were treated with either: (1) cystine-liposomal DNR and chlorpromazine; (2) cystine-liposomal DNR; or (3) nothing. (n=3).

Results from the FACS analysis showed that pre-treatment with 10 μg chlorpromazine caused only a slight reduction of DNR cellular uptake by cells that were treated with 10 μM DNR, and no significant reduction in DNR uptake by cells that were treated with 5 μM cystine liposomal DNR. See FIG. 10A, showing the MFI of DNR fluorescence in cytochalasin D untreated and treated A549 cells that had received either 10 μM or 5 μM Cystine liposomal DNR. One way ANOVA shows relative mean fluorescence intensity of DNR shows significant difference of treatments (F3, 8=85.74; P<0.001). Further analysis of the data by Tukey's post-hoc test in FIG. 10A shows a slight significant increase in relative mean fluorescence intensity of 10 μM cystine liposomal DNR treated with chlorpromazine compared to 10 μM cystine liposomal DNR (P<0.05). The lack of any difference in the cellular uptake of DNR from Cystine liposomal DNR, administered alone, as compared to the uptake of DNR from Cystine liposomal DNR by cells that were pre-treated with chlorprazine, irrespective of whether 10 μM or 5 μM amounts of DNR were added. See FIGS. 10B and 10C.

Example 8

The Effect of Inhibiting Macropinocytosis on DNR Cellular Uptake from Cystine Liposomal DNR Further to the discussion in Example 6 concerning identifying endocytotic mechanisms that may be involved in the cellular uptake of DNR from DNR-loaded cytosine liposomes, amiloride, a specific inhibitor of macropinocytosis, was used in the following DNR uptake studies to determine whether the DNR uptake mechanism from cystine liposomal DNR involved macropinocytosis. These studies were performed by plating A549 cells in triplicate wells of 6-well plates, and treated with cystine liposomal DNR that contained either 10 μm or 5 μm amounts of DNR exactly as described above in Example 3, except that the cells were pre-treated with a 3 mM concentration of amiloride (Sigma-Aldrich) for 30 minutes prior to the introduction of the DNR formulations. FACS analysis of DNR uptake was performed according to the protocol described in Example 3.

Figure 11A:
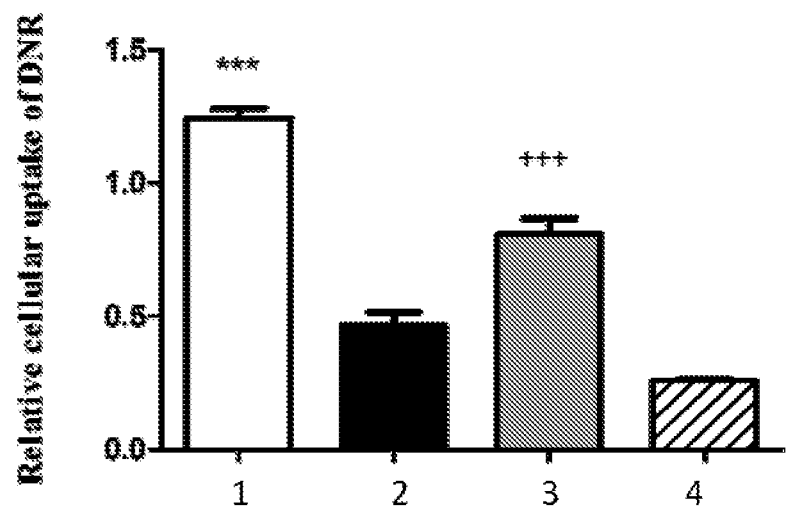
FIG. 11A shows a bar graph of the effect of amiloride (3 mM) on DNR uptake by cells treated with cystine-liposomal DNR formulations that contained either 5 μm or 10 μm doses of DNR. The graph represents the mean fluorescence intensities (MFI) of the different represented DNR formulations based on flow cytometry data. Cellular DNR uptake is expressed as the mean fluorescence intensities of the different represented DNR formulations relative to 10 μM free DNR. Mean and S.E.M are shown. (*$p<0.05$ for cystine-liposomal DNR vs. cystine-liposomal DNR and amiloride are shown for the 5 μM and 10 μM concentrations, n=3). Bar (1) shows DNR uptake following the addition of 10 μm amount of DNR in the form of cystine-liposomal DNR. Bar (2) shows shows DNR uptake in the presence of amiloride following the addition of 10 μm amount of DNR in the form of cystine-liposomal DNR. Bar (3) shows DNR uptake following the addition of 5 μm amount of DNR in the form of cystine-liposomal DNR. Bar (4) shows DNR uptake in the presence of amiloride following the addition of 5 μm amount of DNR in the form of cystine-liposomal DNR.
Figure 11B:
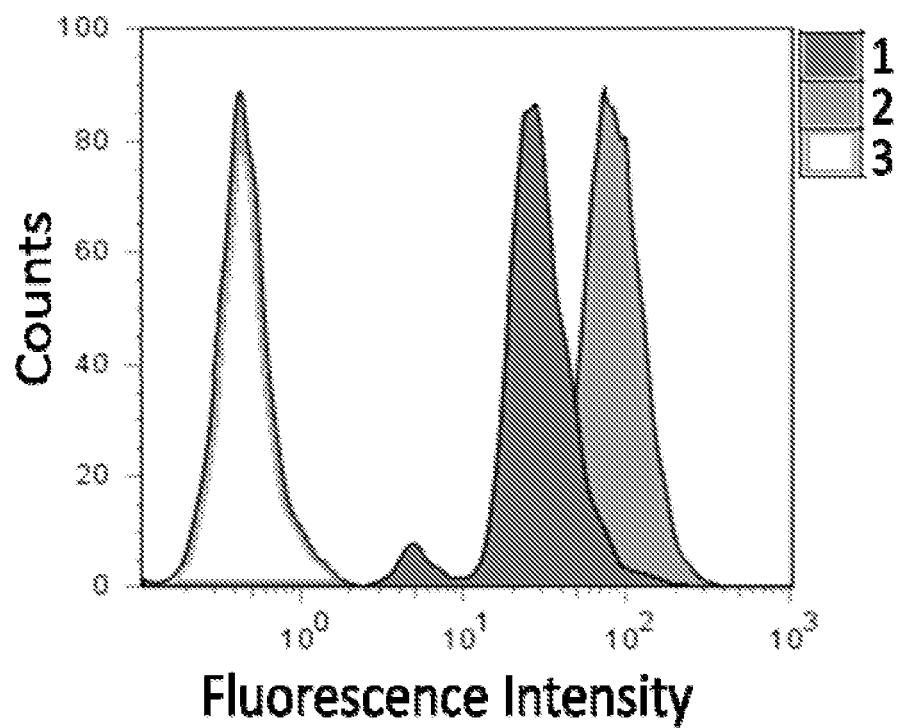
FIG. 11B shows a histogram of the effect of amiloride on DNR uptake by cells treated with a cystine-liposomal DNR formulation that contained a 10 μm dose of DNR. Cell counts versus fluorescence intensities are shown for A549 cells that were treated with either: (1) cystine-liposomal DNR and amiloride; (2) cystine-liposomal DNR; or (3) nothing. (n=3).
Figure 11C:
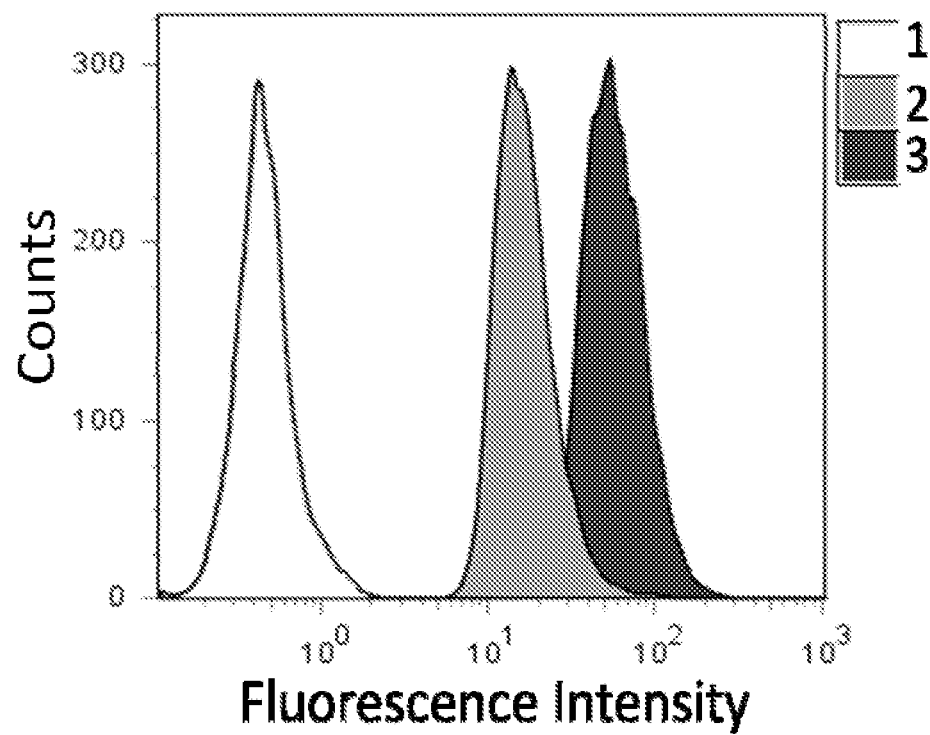
FIG. 11C shows a histogram of the effect of amiloride on DNR uptake by cells treated with a cystine-liposomal DNR formulation that contained a 10 μm dose of DNR. Cell counts versus fluorescence intensities are shown for A549 cells that were treated with either: (1) nothing; (2) cystine-liposomal DNR and amiloride; and (3) cystine-liposomal DNR. (n=3).

Results from the FACS analysis showed that pre-treatment with 3 mM amiloride caused a significant reduction of DNR cellular uptake by cells that were treated with 10 μM DNR or with 5 μM cystine liposomal DNR. See FIG. 11A, showing the MFI of DNR fluorescence in cytochalasin D untreated and treated A549 cells that had received either 10 μM or 5 μM cystine liposomal DNR. One way ANOVA shoes relative mean fluorescence intensity of DNR shows significant difference between the treatments (F3, 8=98.53; P<0.001). Further analysis of the data by Tukey's post-hoc test in FIG. 11A shows a significant decrease in the relative mean fluorescence intensity of cells treated with 10 μM cystine liposomal DNR when the cells are also pre-treated with amiloride versus when the cells receive the cystine liposomal DNR alone (P<0.05). There was also a significant decrease in relative mean fluorescence intensity of cells treated with 5 μM cystine liposomal DNR when the cells are also pre-treated with amiloride versus when the cells receive the cystine liposomal DNR alone. FIGS. 11B and 11C show, in histogram form, the decreases in the cellular uptake DNR by cells that were treated with 10 μM and 5 μM, respectively, cystine liposomal DNR that had been pre-treated with amiloride versus those cells that had only been treated with the cystine liposomal DNR (data used from best of n=3)

Example 9

The Effect of Depleting Cell Membrane Cholesterol on DNR Cellular Uptake from Cystine Liposomal DNR Further to the discussion in Example 6 concerning identifying endocytotic mechanisms that may be involved in the cellular uptake of DNR from DNR-loaded cytosine liposomes, nystatin, a drug that inhibits cholesterol-dependent cellular uptake, was used in the following DNR uptake studies to determine whether the DNR uptake mechanism from cystine liposomal DNR involved cell membrane cholesterol. These studies were performed by plating A549 cells in triplicate wells of 6-well plates, and treated with cystine liposomal DNR that contained either 10 μm or 5 μm amounts of DNR exactly as described above in Example 3, except that the cells were pre-treated with a 100 μg/ml concentration of nystatin (Sigma-Aldrich) for 30 minutes prior to the introduction of the DNR formulations. FACS analysis of DNR uptake was performed according to the protocol described in Example 3.

Figure 12A:
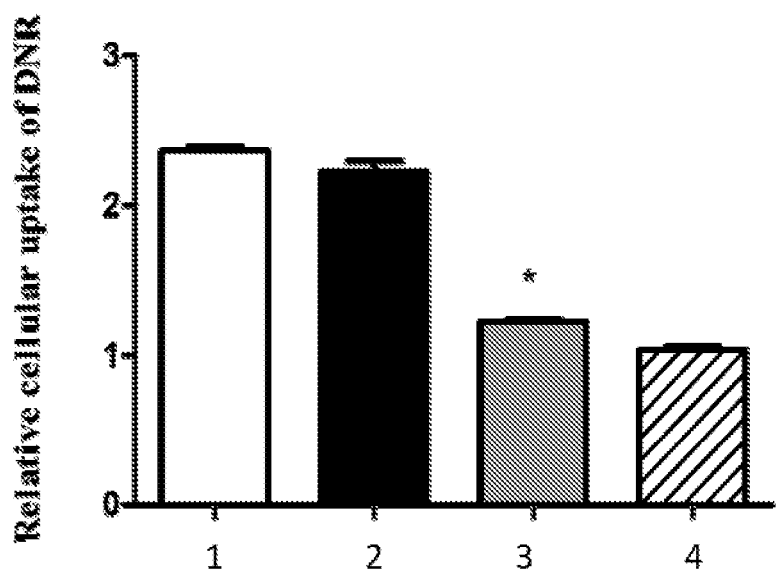
FIG. 12A shows a bar graph of the effect of nystatin (100 μg/ml) on DNR uptake by cells treated with cystine-liposomal DNR formulations that contained either 5 μm or 10 μm doses of DNR. The graph represents the mean fluorescence intensities (MFI) of the different represented DNR formulations based on flow cytometry data. Cellular DNR uptake is expressed as the mean fluorescence intensities of the different represented DNR formulations relative to 10 μM free DNR. Mean and S.E.M are shown. (*$p<0.05$ for cystine-liposomal DNR vs. cystine-liposomal DNR and nystatin is based on the 5 μM concentrations, n=3). Bar (1) shows DNR uptake following the addition of 10 μm amount of DNR in the form of cystine-liposomal DNR. Bar (2) shows DNR uptake in the presence of nystatin following the addition of 10 μm amount of DNR in the form of cystine-liposomal DNR. Bar (3) shows DNR uptake following the addition of 5 μm amount of DNR in the form of cystine-liposomal DNR. Bar (4) shows DNR uptake in the presence of nystatin following the addition of 5 μm amount of DNR in the form of cystine-liposomal DNR.
Figure 12B:
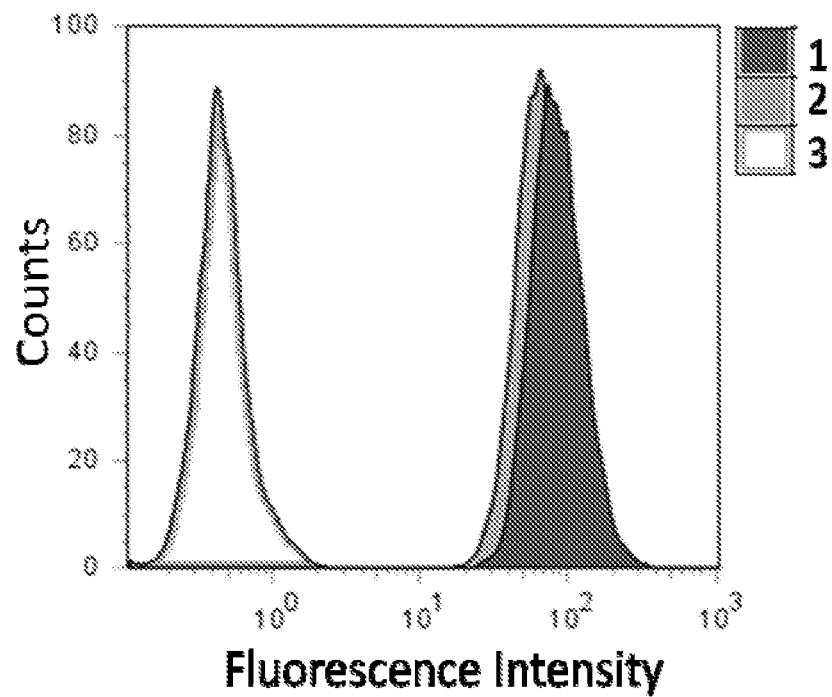
FIG. 12B shows a histogram of the effect of nystatin on DNR uptake by cells treated with a cystine-liposomal DNR formulation that contained a 10 μm dose of DNR. Cell counts versus fluorescence intensities are shown for A549 cells that were treated with either: (1) cystine-liposomal DNR; (2) cystine-liposomal DNR and nystatin; or (3) nothing. (n=3).
Figure 12C:
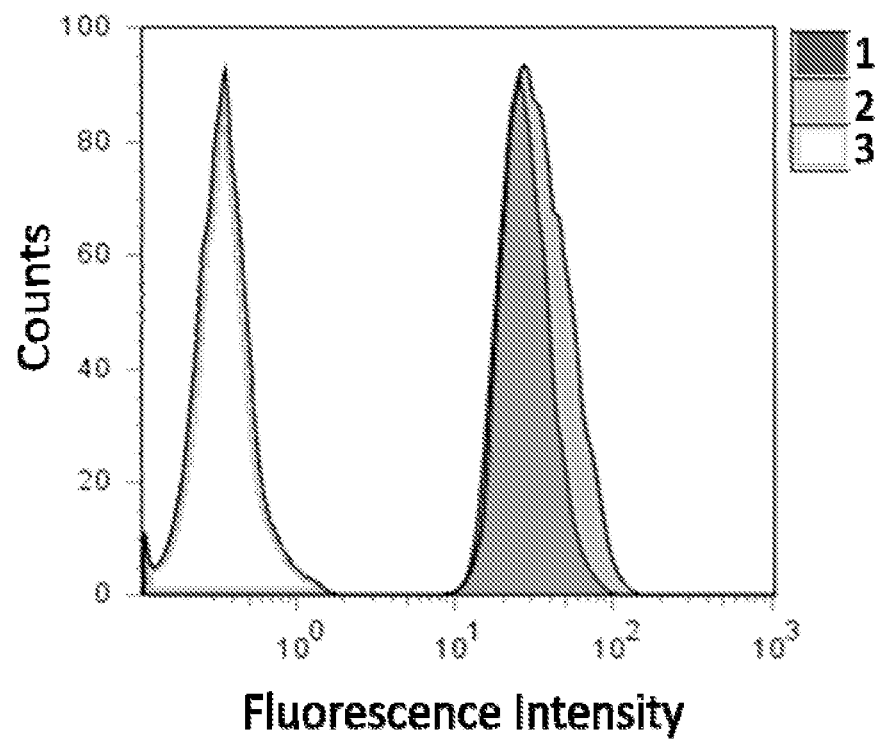
FIG. 12C shows a histogram of the effect of nystatin on DNR uptake by cells treated with a cystine-liposomal DNR formulation that contained a 10 μm dose of DNR. Cell counts versus fluorescence intensities are shown for A549 cells that were treated with either: (1) cystine-liposomal DNR; (2) cystine-liposomal DNR and nystatin; or (3) nothing. (n=3).
Figure 13A:
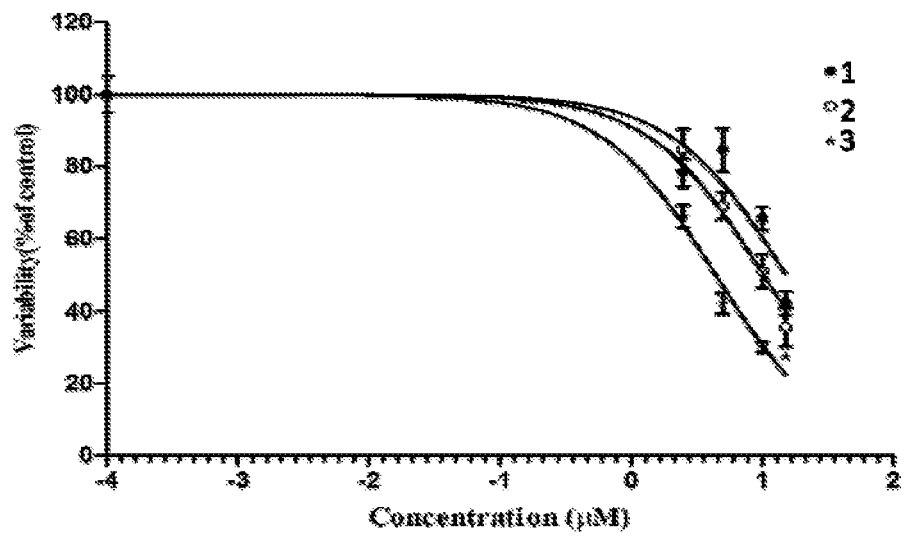
FIG. 13A shows a line graph of A549 cell growth inhibition curves for free-DNR, and cystine-liposomal DNR. The $IC_{50}$ DNR concentrations for (1) cystine-liposomal DNR, (2) liposomal DNR, and (3) free DNR are 4.435 μM, 10.25 μM, and 15.25 μM, respectively.

Results from the FACS analysis showed that pre-treatment with 100 μg/ml nystatin caused no significant reduction of DNR cellular uptake by cells that were treated with 10 μM DNR, or 5 μM cystine liposomal DNR. See FIG. 12A, showing the MFI of DNR fluorescence in nystatin untreated and treated A549 cells that had received either 10 μM or 5 μM cystine liposomal DNR. One way ANOVA shows relative mean fluorescence intensity of DNR shows significant difference of treatments (F3, 8=271.8; P<0.001). Further analysis of the data by Tukey's post-hoc test in FIG. 12A shows no significant difference in relative mean fluorescence intensity of in the relative mean fluorescence intensity of cells treated with 10 μM cystine liposomal DNR when the cells are also pre-treated with nystatin versus when the cells receive the cystine liposomal DNR alone. Also, shows a slight significant decrease in relative mean fluorescence intensity of cells that were treated with 10 μM cystine liposomal DNR that had been pre-treated with nystatin compared to the celld that had only been treated with 10 μM Cystine liposomal DNR (P<0.05). FIGS. 12B and 12C show slight decrease in the cellular uptake of DNR from 10 μM or 5 μM cystine liposomal DNR that had been pre-treated with nystatin compared to those cells that had only received the cystine liposomal DNR.

Example 10

DNR-Mediated Cytotoxicity Following Treatment with Cystine Liposomal DNR

Because DNR is a cytotoxic compound, the effectiveness of cystine liposomal DNR as an intracellular delivery system was assessed by relying on cytotoxicity measurements as a measure of DNR uptake. Controls for cystine liposomal DNR included free DNR and Liposomal DNR that did not contain cystine. Cytotoxicity was measured in A549 cells following the addition of the aforementioned DNR formulations to the cells followed by an incubation period, and determination of cytotoxicity by using a MTS assay. Briefly, an MTS assay is a non radioactive cell proliferative assay of a tetrazolium compound (3-(4,5-dimethylthiazol-2-yl)-5-(3-carboxymethoxyphenyl)-2-(4-sulfophenyl)-2H-tetrazolium, inner salt; MTS) and the electron coupling reagent, phenazine methosulfate (PMS). MTS is bio-reduced by cells to a formazan compound by a reductase enzyme present in metabolically active cells. The absorbance of the formazan compound can be measured at 490 nm wavelength and is directly proportional to the number of living cells. The toxicity was determined using dose response curve to determine $IC_{50}$. $IC_{50}$ is the concentration of the test compound required to reduce light absorbance capacity of the cells by 50%.

MTS reagent was prepared by mixing 20% MTS and 1% PMS solution in RPMI 1640 medium of volume 8 ml. After removal of the growth medium from the wells, 100 μl of this prepared MTS reagent was added to each well and incubated for 4 hr at 37° C. in humidified atmosphere of 5% $CO_2$. MTS reduces to colored formazan product by the living cells, and is soluble in the medium. The amount of formazan was measured at 490 nm wavelength.

Figure 13B:
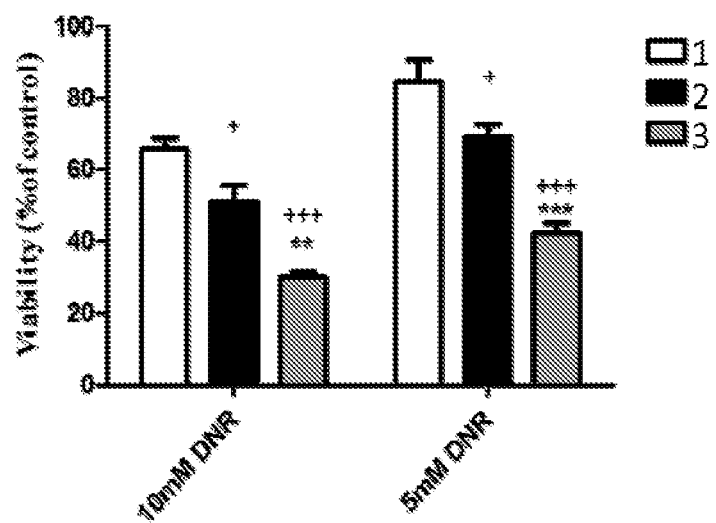
FIG. 13B shows a bar graph of the percentages of A549 cells that were viable following treatments with (1) free DNR, (2) liposomal DNR, or (3) cystine-liposomal DNR formulations that contained dosage amounts of DNR equivalent to either 5 μM or 10 μM of DNR. (+++$p<0.001$ based on the 5 μM and 10 μM DNR formulations of cystine-liposomal DNR versus the 5 μM and 10 μM DNR formulations of free DNR, +$p<0.01$ based on the 5 μM and 10 μM DNR formulations of liposomal DNR versus the 5 μM and 10 μM DNR formulations of free drug, $p<0.01$ based on the 10 μM DNR formulation of cystine liposomal DNR vs. the 10 μM DNR formulation of liposomal DNR, and *$p<0.001$ is based on the 5 μM DNR formulation of cystine liposomal DNR versus the 5 μM DNR formulation of liposomal DNR.) Mean and S.E.M are shown. (n=3).

A dose-response curve for the DNR-loaded liposome formulation was made by plating $5 \times 10^3$ cells that were suspended in 100 μl of RPMI medium into each well of a 96-well plate, and incubating the cells for 24 hr at 37° C. in humidified atmosphere of 5% $CO_2$. After incubation, the cells were pre-treated for 30 minutes with 5 mM of the cystine uptake inhibitor, glutamate, as described in Example 4. Control wells for glutamate addition were covered only in 50111 of RPMI medium. Incubation at 37° C. in humidified atmosphere of 5% $CO_2$ was for half an hour. The DNR-loaded cystine liposome, free DNR, and Liposomal DNR were serially diluted such that the final DNR concentrations of the dilution series were 2.5 μM DNR, 5 μM DNR, 10 μM DNR, and 15 μM DNR in totals suspended in 200 ul/well in three replicated wells for 72 hours. The first rows of each side of the plate were not plated with cells and used in the assay, but were filled with 100 μl of PBS to minimize any contamination or evaporation instead. Dose response curves were plotted using the Prism™ software (San Diego, Calif.). Each experiment was performed twice independently. The $IC_{50}$ data are reported in FIG. 13A. FIG. 13B shows the viability of the A549 cells after 72 hours of treatment with either free DNR, Liposomal DNR, or cystine liposomal DNR.

Table 1 shows $IC_{50}$ concentrations for the free DNR and cystine liposomal DNR and DNR loaded liposomes, The $IC_{50}$ concentrations for the free DNR, liposomal DNR and cystine liposomal DNR was 15.25 μM, 10.25 μM and 4.44 μM, respectively. See also, FIG. 13A. The $IC_{50}$ of liposomal DNR was 1.5 fold lower than the $IC_{50}$ of free DNR, which means that liposomal DNR are more cytotoxic than free DNR. The $IC_{50}$ of cystine liposomal DNR was 3.5 fold and 2.3 fold lower than the $IC_{50}$ of free DNR and Liposomal DNR, respectively, which correlated to an increase in cytotoxicity.

Figure 14A:
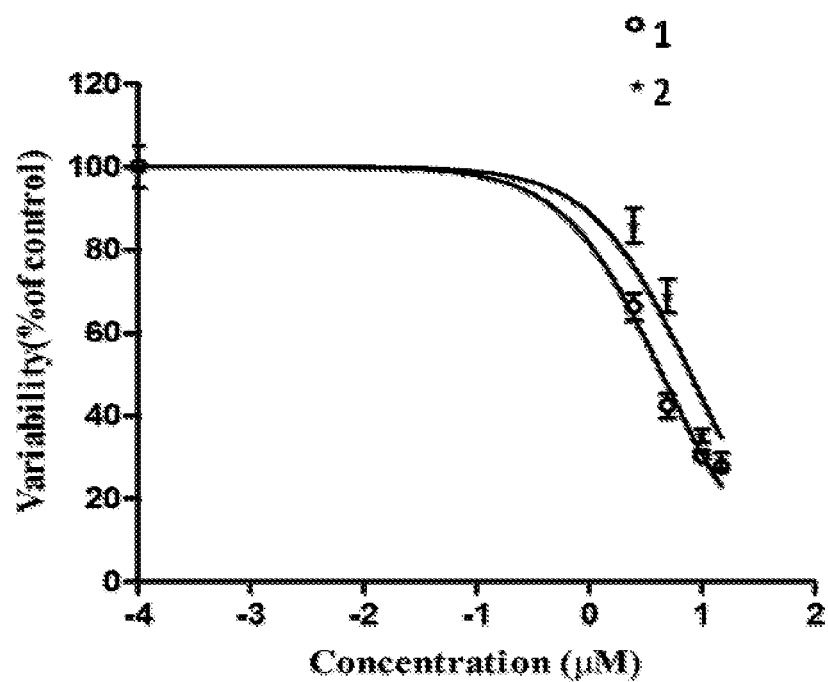
FIG. 14A shows a line graph of the effect of glutamate on A549 cell growth inhibition mediated by cystine-liposomal DNR. The $IC_{50}$ DNR concentrations for: (1) cystine-liposomal DNR; and (2) cystine-liposomal DNR are 4.435 μM and 7.947 μM, respectively.
Figure 14B:
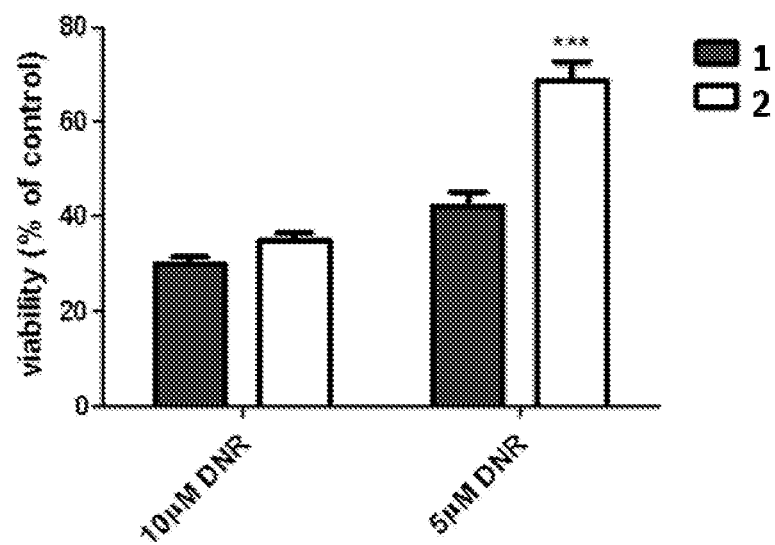
FIG. 14B shows a bar graph of the percentages of A549 cells that were viable following treatments with cystine-liposomal DNR, and (2) cystine-liposomal DNR formulations that contained dosage amounts of DNR equivalent to either 10 μM or 5 μM of DNR. (***$p<0.001$ based on the 5 μM DNR formulation of cystine-liposomal DNR versus the 5 μM DNR formulation of cystine-liposomal DNR cystine-liposomal DNR plus glutamate) Mean and S.E.M are shown. (n=3).

The $IC_{50}$ concentration of cystine liposomal DNR increases significantly when the A549 cells are pre-treated with 5 mM glutamate, as described in Example 4. See Table 1 and FIG. 14A. The graph shown at FIG. 14B shows the viability of cells for 10 μM and 5 μM concentrations free DNR, liposomal DNR, and cystine liposomal DNR in the absence and presence of pre-treatment with 5 mM glutamate. ***p<0.0.001 is 5 μM cystine liposomal DNR vs. 5 μM cystine liposomal DNR+glutamate.

TABLE 1

| Formulation | IC$_{50}$(μM) | |
| --- | --- | --- |
| | AVG | S.E. |
| Free DNR | 15.25 | 0.03400 |
| Liposomal DNR | 10.25 | 0.08190 |
| Cystine liposomal DNR | 4.435 | 0.03483 |
| Cystine liposomal DNR + glutamate | 7.947 | 0.07915 |

Figure 15:
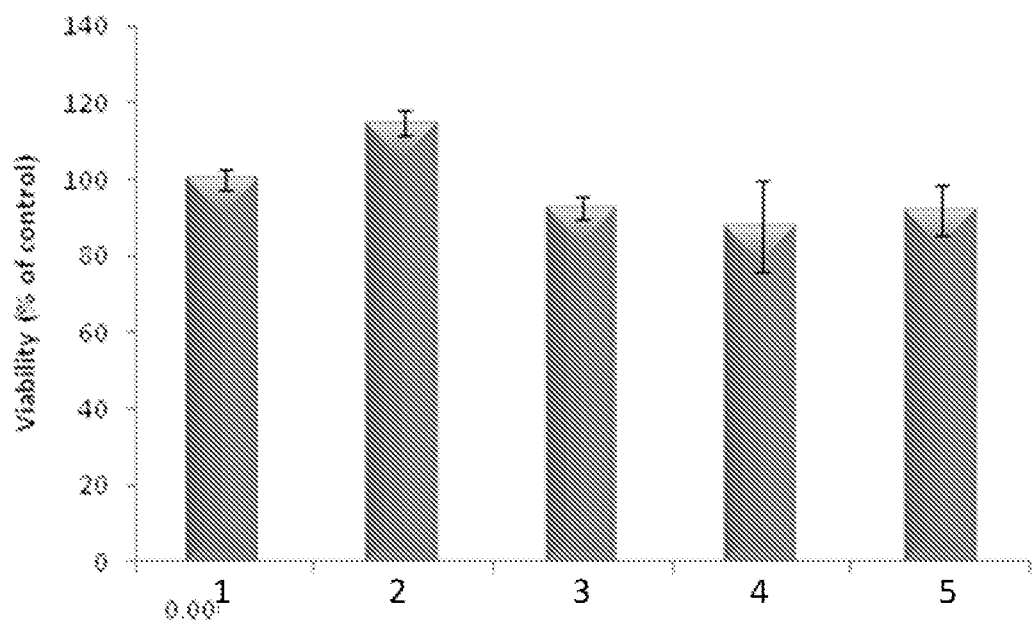
FIG. 15 shows a bar graph of the correlation between the amount of DNR that was added in the form of liposomal DNR and cell viability after 72 hours of treatment. Bar (1) shows 0.0001 μM liposomal DNR, Bar (2) shows 2.5 μM liposomal DNR, Bar (3) shows 5 μM liposomal DNR, Bar (4) shows 10 μM liposomal DNR, and Bar (5) shows 15 μM liposomal DNR.
Figure 16:
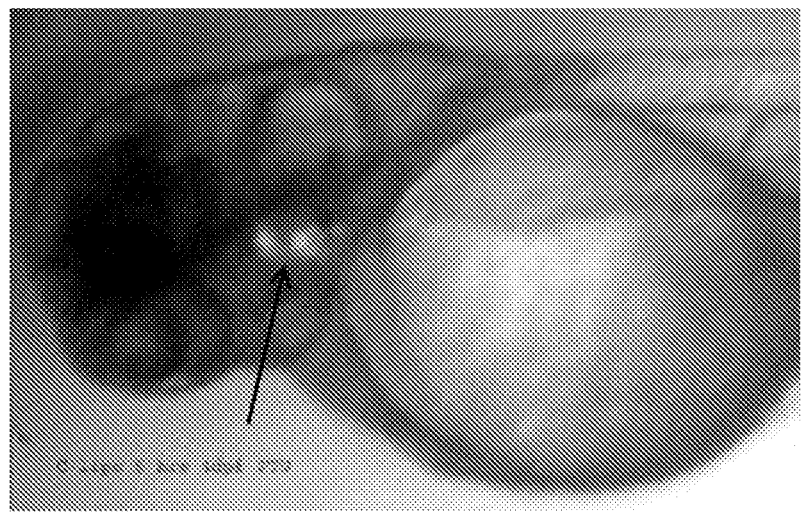
FIG. 16 shows fluorescence images of the delivery of DNR to the stomach in pharyngula-stage zebrafish embryos that were allowed to ingest cystine liposomal DNR (A) versus zebrafish embryos that were allowed to ingest liposomal DNR (B). The arrow in panel 16A points to DNR that remained in the stomach of the zebrafish.
Figure 16:
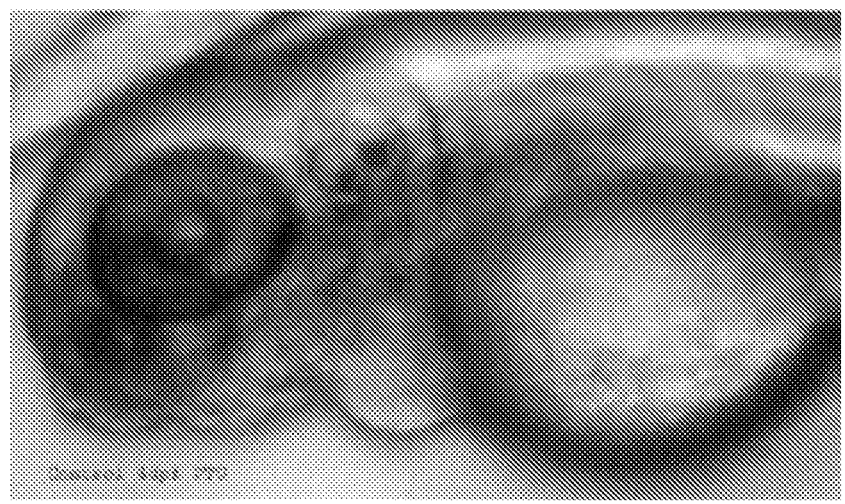

Two way ANOVA showed significant effect of concentration (F1, 12=25.99; p<0.001), and significant effect of the free DNR, DNR-loaded liposome, and DNR-loaded cystine liposome formulations (F2, 12=49.52; p<0.001). There was no significant correlation between the amount of DNR that was added in the form of liposomal DNR and cell viability. In particular, neither 0.0001, 2.5, 5, 10, and 15 μM concentrations of Liposomal DNR had an effect on cell viability of A549 cells after 72 hours of treatment with the liposomal DNR formulations. See FIG. 15. There was also a significant difference between liposomal DNR and free DNR for both concentrations (10 μM and 5 μM) (P<0.05).

Example 11

Zebrafish Studies

The capacity of cystine liposomal DNR to deliver DNR in vivo was assessed by tracking DNR in the gastrointestinal tracts of pharyngula-stage zebrafish that were allowed to ingest either cystine liposomal DNR or liposomal DNR. The arrow in panel 16A points to DNR that remained in the stomach of the zebrafish.

Example 12

In Vivo Tumor Studies

In view of the fact that SLC7A11 is upregulated in cancerous cells of pancreatic, lung, prostate, and stomach origins, the potential of Cystine liposomal DNR to deliver DNR to tumor cells were performed as follows. Female C57BL/6J wild-type mice, aged 8 weeks, were purchased from Jackson Laboratories (Bar Harbor, Me.). Animals were housed with ad libitum access to food and water in a pathogen free facility, and were acclimatized for one week before being included in these studies. Subcutaneous tumors were established by subcuntaneous injection of 1×10$^6$ cells of a syngenic pancreatic tumor cell line (Pan02, NCI, Frederick, Md.) into the right flanks of the mice by using a 27 gauge needle. When the tumors became palpable, the mice were randomized into five treatment groups of n=7. The ranges of tumor sizes for each group of mice was equivalent. On day one of the study, the five groups of mice were injected in the tail vein with either: 1) Saline; 2) Free 5 mg/kg body weight DNR; 3) Liposomal DNR (5 mg DNR/kg body weight); 4) Cystine liposomal DNR (5 mg DNR/kg body weight); or 5) Pegylated Cystine liposomal DNR (5 mg DNR/kg body weight), respectively. Tumor sizes were measured every 2 to 3 days for 17 days from day of treatment by using digital Vernier Calipers in two dimensions. The mice were sacrificed on day 20 of the assay, and the tumors were measured once again. Tumor volume was calculated using the following equation: $V=\pi/6 \times L \times W^2$, wherein L=Longest dimension, and W=shortest dimension. All the data were analyzed by Two-way ANOVA with Bonferroni post-test to compare between groups. (n=7).

Figure 17A:
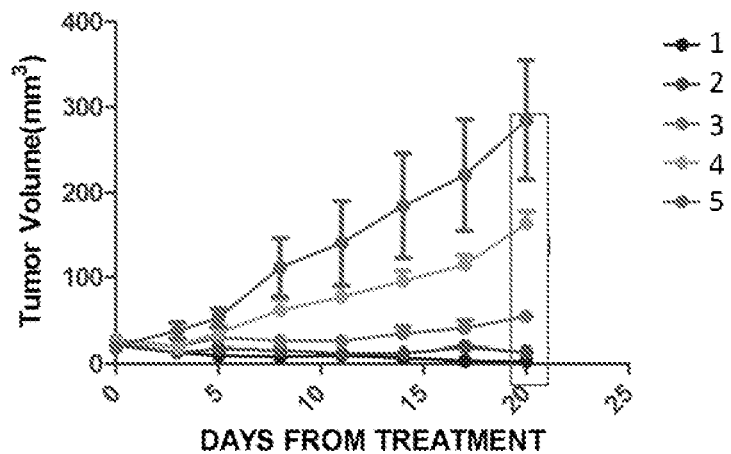
FIG. 17A shows the effect over time of the following DNR formulations on tumor volume in a Pan02 cell in vivo tumor model: (1) Pegylated cystine liposomal DNR; (2) Cystine liposomal DNR; (3) Liposomal DNR; (4) Free DNR; and (5) Saline.
Figure 17B:
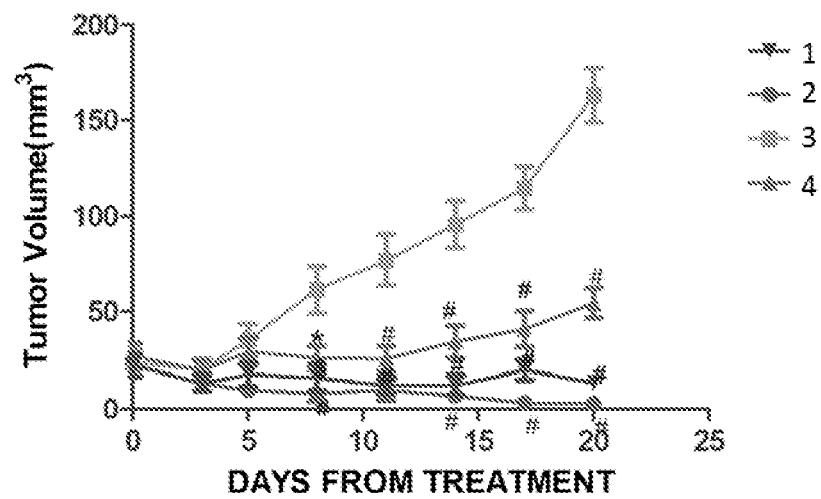
FIG. 17B shows a line graph of the effect of the DNR formulations of FIG. 17A in greater detail. (1) Cystine liposomal DNR; (2) Pegylated cystine liposomal DNR; (3) Free DNR; and (4) Liposomal DNR.
Figure 17:
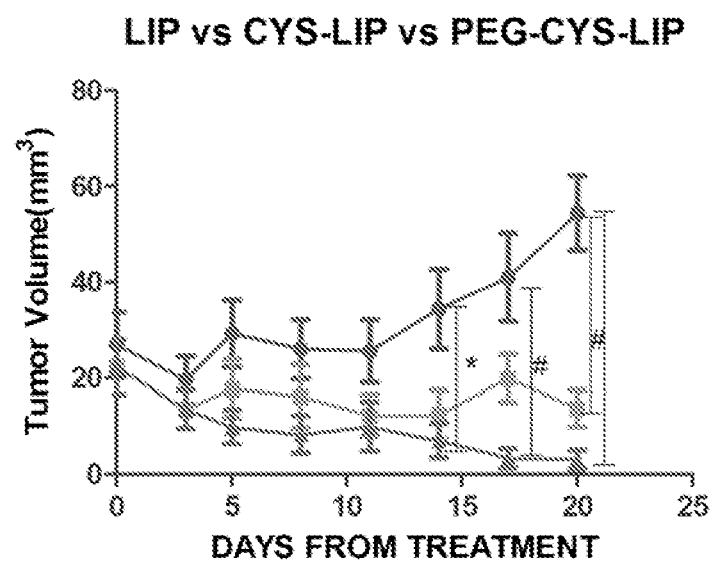
FIG. 17C shows the anti-tumor effects of the liposome-based DNR formulations of FIG. 17A. (1) Liposomal DNR; (2) Cystine liposomal DNR; and (3) Pegylated cystine liposomal DNR.
FIG. 17D shows the effect on body weights of: (1) Saline; (2) Free DNR; (3) Liposomal DNR; (4) Cystine liposomal DNR; and (5) Pegylated cystine liposomal DNR.
Figure 17:
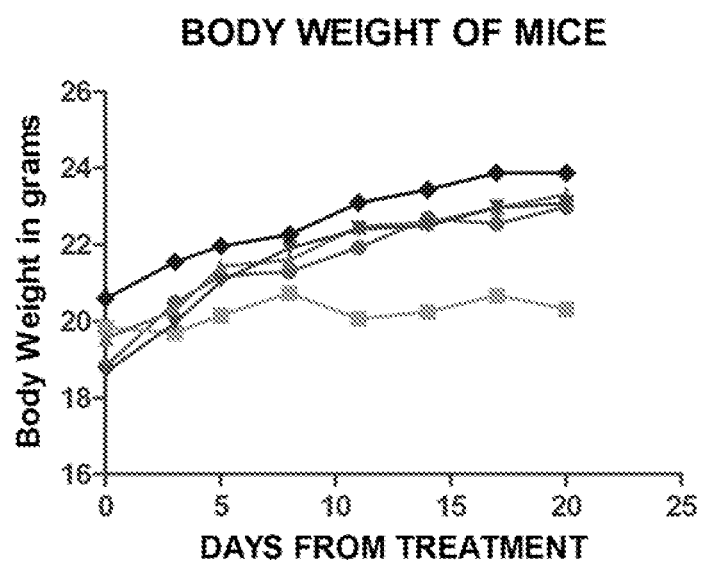

Treatment of the tumors with the cystine liposomal DNR significantly reduced the tumor size in animals compared to treatment with either liposomal DNR or nonencapsulated (free) DNR. See FIG. 17A-C. An even more significant reduction in tumor sizes was achieved by Pegylated Cystine liposomal DNR. The PEG component of the pegylated Cystine liposomal DNR was added to evade recognition from phagocytic cells. PEGylated cystine liposomes were made by using the post insertion technique. Briefly, solution of 1,2-distearoyl-sn-glycero-3-phosphoethanolamine (DSPE)-mPEG2000 (Avanti Polar Lipids Inc. Alabaster, Ala., USA) was mixed with cystine liposomes and left to incubate for a few hours to allow for the insertion of DSPE-mPEG2000 into the preformed liposomes. This suspension was then extruded 12 times using LIPEX extruder, lyophilized, and frozen at −80° C. until use.

Body weights were also measured at the time tumor measurements were made, to use as indicators of the animals' overall health. As judged based on the body weights of the mice over the course of the study, the adverse effects of the liposomal formulations, i.e., liposomal DNR, cystine liposomal DNR, and pegylated cystine DNR, were reduced in comparison to the adverse effects of free DNR. See FIG. 17D.

The claimed invention is:

1. A vehicle for the targeted intracellular delivery of a therapeutic agent or a diagnostic agent, or both, the vehicle comprising a cystine molecule coupled to a cargo, wherein the cargo is a liposome composition comprising a therapeutic agent, a diagnostic agent, or both, wherein the cystine is a targeting component.

2. A vehicle of claim 1, wherein the cystine molecule is coupled to the cargo directly by a chemical bond.

3. A vehicle of claim 1, wherein the cystine molecule is coupled to the cargo by a linking group.

4. A vehicle of claim 3, wherein the linking group is a polyethylene glycol molecule.

5. A vehicle of claim 1, wherein the therapeutic agent is selected from the group consisting of inorganic molecules, therapeutic peptides and proteins, antibodies, radioisotopes, siRNA and nucleic acids for gene therapy, toxins, and anti-cancer agents.

6. A vehicle of claim 1, wherein the diagnostic agent is selected from a fluorescent substance, an electron dense substance, a reporter moiety, a specific binding moiety, and a radioactive substance.

7. A method for improving the intracellular delivery of a therapeutic or diagnostic composition, comprising the step of administering composition of claim 1.

8. A pharmaceutical formulation comprising:
 a) a vehicle for the targeted intracellular delivery of a therapeutic agent, a diagnostic agent, or both, the vehicle comprising a cystine molecule coupled to a cargo for intracellular delivery, wherein the cargo is a liposome composition comprising a therapeutic agent, a diagnostic agent, or both, wherein the cystine is a targeting component; and
 b) a pharmaceutically acceptable carrier.

* * * * *